United States Patent
Jia et al.

(10) Patent No.: US 10,123,689 B2
(45) Date of Patent: Nov. 13, 2018

(54) SYSTEMS AND METHODS FOR RETINAL LAYER SEGMENTATION IN OCT IMAGING AND OCT ANGIOGRAPHY

(71) Applicants: Yali Jia, Portland, OR (US); David Huang, Portland, OR (US); Miao Zhang, Portland, OR (US)

(72) Inventors: Yali Jia, Portland, OR (US); David Huang, Portland, OR (US); Miao Zhang, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 15/333,778

(22) Filed: Oct. 25, 2016

(65) Prior Publication Data
US 2017/0119242 A1 May 4, 2017

Related U.S. Application Data

(60) Provisional application No. 62/247,337, filed on Oct. 28, 2015.

(51) Int. Cl.
| | |
|---|---|
| G06K 9/00 | (2006.01) |
| A61B 3/00 | (2006.01) |
| A61B 3/10 | (2006.01) |
| G06T 7/00 | (2017.01) |
| G06T 7/11 | (2017.01) |
| G06T 11/60 | (2006.01) |
| G06T 7/162 | (2017.01) |
| G06T 7/181 | (2017.01) |

(52) U.S. Cl.
CPC .......... *A61B 3/0025* (2013.01); *A61B 3/102* (2013.01); *A61B 3/1005* (2013.01); *G06T 7/0012* (2013.01); *G06T 7/11* (2017.01); *G06T 7/162* (2017.01); *G06T 7/181* (2017.01); *G06T 11/60* (2013.01); *G06T 2207/10101* (2013.01); *G06T 2207/30041* (2013.01)

(58) Field of Classification Search
CPC ..... A61B 3/0025; A61B 3/1005; A61B 3/102; A61B 3/1233; G06T 11/60; G06T 2207/10101; G06T 2207/30041; G06T 7/0012; G06T 7/11; G06T 2207/30104; G06T 7/162; G06T 7/181; G06T 7/90
USPC ....................................................... 382/128
See application file for complete search history.

(56) References Cited

U.S. PATENT DOCUMENTS

| | | |
|---|---|---|
| 8,693,749 B2 | 4/2014 | Nakano |
| 9,113,779 B2 | 8/2015 | Sakagawa et al. |
| 9,582,732 B2 | 2/2017 | Pintal et al. |

(Continued)

OTHER PUBLICATIONS

Srinivasan et al., "Automatic segmentation of up to ten layer boundaries in SD-OCT images of the mouse retina with and without missing layers due to pathology," Biomedical Optics Express 5, 348-365 (2014).
Chiu et al., "Automatic segmentation of seven retinal layers in SDOCT images congruent with expert manual segmentation," Optics Express 18, 19413-19428 (2010). Yin et al., "User-guided segmentation for volumetric retinal optical coherence tomography images," Journal of Biomedical Optics 19, 086020-086020 (2014).

(Continued)

*Primary Examiner* — Tom Y Lu

(57) ABSTRACT

Disclosed herein are methods and systems for segmenting, visualizing, and quantifying the layered structure of retina in optical coherence tomography datasets. The disclosed methods have particular application to OCT angiography data, where specific retina layers have distinct vascular structures and characteristics that can be altered in various pathological conditions of the eye.

3 Claims, 18 Drawing Sheets

(56) References Cited

U.S. PATENT DOCUMENTS

| | | |
|---|---|---|
| 9,928,602 B2 | 3/2018 | Ren et al. |
| 2005/0018133 A1 | 1/2005 | Huang et al. |
| 2015/0366450 A1 | 12/2015 | Ren et al. |
| 2015/0371400 A1 | 12/2015 | Farsiu et al. |
| 2017/0098311 A1 | 4/2017 | Abramoff et al. |
| 2017/0109883 A1 | 4/2017 | Lowry et al. |
| 2017/0132793 A1 | 5/2017 | Hu et al. |
| 2017/0140544 A1* | 5/2017 | Farsiu ................. G06T 7/11 |
| 2017/0164825 A1 | 6/2017 | Chen et al. |

OTHER PUBLICATIONS

Mortensen et al., "Intelligent scissors for image composition," in Proceedings of the 22nd Annual Conference on Computer Graphics and Interactive Techniques(ACM, 1995), pp. 191-198.

Liu et al., "Optimal Graph Search Based 5 Segmentation of Airway Tree Double Surfaces Across Bifurcations," Medical Imaging, IEEE Transactions on 32, 493-510 (2013).

Merickel et al., "Segmentation of the optic nerve head combining pixel classification and graph search," in Medical Imaging(International Society for Optics and Photonics, 2007), pp. 651215-651215-651210.

Garvin et al., "Intraretinal layer segmentation of macular optical coherence tomography images using optimal 3-D graph search," Medical Imaging, IEEE Transactions on 27, 1495-1505 (2008).

Chen et al., "Three dimensional segmentation of fluid-associated abnormalities in retinal OCT: probability constrained graph-search-graph-cut," Medical Imaging, IEEE Transactions on 31, 1521-1531 (2012).

* cited by examiner

SYSTEMS AND METHODS FOR RETINAL LAYER SEGMENTATION IN OCT IMAGING AND OCT ANGIOGRAPHY

ACKNOWLEDGEMENT OF GOVERNMENT SUPPORT

This invention was made with the support of the United States government under the terms of Grant Number R01 EY023285, R01 EY024544, and DP3 DK104397 awarded by the National Institutes of Health. The United States government has certain rights in this invention.

FIELD

Generally, the field involves methods of using optical coherence tomography (OCT) to image and segment the layers of the retina. More specifically, the field involves methods of processing OCT datasets to visualize and quantify vascular structures in the retina for both normal and pathologic conditions.

BACKGROUND

Optical coherence tomography (OCT) is a noninvasive, depth resolved, volumetric imaging technique that provides cross-sectional and three-dimensional (3D) imaging of biological tissues. OCT is commonly used to visualize retinal morphology and has become a part of the standard of care in ophthalmology [1, 2]. A limitation of conventional structural OCT, however, is that it is only sensitive to backscattered light intensity and is thus unable to directly detect blood flow or discriminate vascular tissue from its surrounding tissue. This limits the utility of structural OCT to detect blood flow abnormalities such as capillary dropout or pathologic vessel growth (neovascularization), which are the major vascular abnormalities associated with two of the leading causes of blindness, age-related macular degeneration (AMD) and proliferative diabetic retinopathy (PDR). Current standard-of-care techniques to visualize these abnormalities, fluorescein angiography (FA) or indocyanine green (ICG) angiography, require the use of an intravenous dye-based contrast agent, which can increase the risk of complications or adverse reactions and increases the amount of time required for imaging.

OCT angiography is a refinement of the OCT imaging technique that uses the motion of red blood cells against static tissue as intrinsic contrast to allow visualization of blood flow. Several OCT angiography methods have been proposed in the literature [3-7]. These OCT angiography methods enable high resolution imaging of microvascular networks and can be implemented using commercial OCT devices designed for structural OCT imaging [8, 9]. En face projection of OCT angiography-derived blood flow results onto a single plane can be used to present the clinician with angiogram images that are analogous to traditional FA and ICG angiography [10, 11].

OCT angiography has been used to quantify vessel density and flow index [12-15], choroidal neovascularization (CNV) area [16, 17], and detect retinal neovascularization (RNV) [15, 18] and macular ischemia. These analyses require accurate segmentation of the retina for proper interpretation and quantification of 3D angiograms. The simplest method of segmentation involves manual delineation of retina layer boundaries by an experienced expert, but this approach is subjective, operator intensive, and time-consuming. Automated segmentation algorithms have been proposed, but these approaches can fail in datasets exhibiting pathologies such as drusen, cystoid macular edema, subretinal fluid or pigment epithelial detachment that distort the normal tissue boundaries. Such segmentation errors necessitate manual correction approaches, but these approaches can be tedious and inefficient [19]. Thus, there remains a need for robust methods and tools to segment the retinal layers for interpretation and quantification of angiograms.

SUMMARY

Disclosed herein are methods and systems for the segmentation of the layered structure of the retina as depicted in OCT scans. Included are methods for both automated segmentation of retinal layers and manual correction of segmented layer boundaries. An aspect of the disclosed systems and methods is that they can be used to separate 3D OCT angiography blood flow data into different layers to facilitate analysis and visualization of ocular abnormalities including, but not limited to, retinal and choroidal neovascularization, retinal ischemia, and macular edema.

According to one aspect, segmentation is performed on the structural OCT scan to delineate anatomic boundaries of retinal layers and blood flow is extracted from OCT angiography data; these data can be merged and presented in a color-coded format as composite images to associate blood flow data with specific structural layers of the retina. Merged data can be presented in three-dimensional form, as two-dimensional cross sections, or as 2D en face maximum projection angiograms, all suitable for qualitative and quantitative assessment of the retina.

An approach for automated segmentation of the layers of the retina based on a directional graph search is disclosed. In an embodiment, a graph search technique is applied to a B-scan image of a retinal cross section such that the search space is constrained to move in a "left-to-right" manner (i.e., proceeding laterally with no reversal of the search trajectory) and large steps perpendicular to the retinal layer directions are minimized. By limiting the search space of the graph search to proceed in a directional manner, computation time is minimized and the layer-wise structure of the retinal anatomy is more faithfully reproduced. Within a given B-Scan, multiple layer boundaries are segmented serially in a specified order, with the results of a given layer boundary segmentation used to constrain the search space for subsequent layer boundaries within the same B-scan. Constrain of the successive search space provides improved segmentation performance, both in terms of anatomic fidelity and computational speed. Segmentation performance can further be enhanced for the entire 3D volumetric data set by propagating information from the segmented layer boundaries of a given B-scan to its adjacent unsegmented B-scan image. Such propagation of layer segmentation data serves constrain the directional graph search space to be performed on the next B-scan, thereby increasing the computational efficiency of the segmentation process. This segment-propagate process can be repeated across all B-scans of the OCT data set in a loop-wise manner to generate surfaces within the 3D dataset that represent layer boundaries.

In an embodiment, a pre-processing procedure can be implemented to handle datasets with highly curved retina profiles. Such a pre-processing step can be advantageous when segmenting data sets that cover a wide-field of view, as those that might be acquired by modern swept source OCT systems. Such highly curved profiles have the potential to yield suboptimal segmentation results with the directed graph search method. Disclosed herein is a flattening procedure which can be applied to transform 3D datasets into a more planar profile prior to segmentation. Once segmentation of the retinal layer boundaries is complete, transformation back to the original configuration recovers the properly segmented boundaries delineating the retinal layers.

According to another aspect, methods are disclosed to enable manual editing of segmentation results. In an embodiment directional graph search can be incorporated into manual editing functionality to allow user-guided segmentation of layers or correction of areas where automated segmentation has failed or is not optimal. In the latter case, in an embodiment, an expert user can choose to post-process segmentation results to re-route a given layer segmentation, or portion thereof, by manually specifying a set of points through which the layer boundary should pass; the directional graph search is then used to calculate a minimum cost new segmentation path that is constrained to pass through said user-supplied points.

In an alternative embodiment of manual editing, a fully interactive version of layer boundary segmentation can be implemented wherein an expert user supplies a starting point (using a mouse device, for example) and then moves the cursor forward by a variable distance, whereupon a minimum cost boundary is calculated and "snapped" to intervening pixels based on the results of directed graph search conducted in real time. In this embodiment, the user can proceed left to right across the image, specifying intermediate starting points as needed, to trace the layer boundary in a semi-automated manner. In such an "intelligent scissors"-inspired approach, individual boundary layers within a B-scan can be segmented quickly and reliably with less susceptibility to noise than would be encountered in in a purely manual outlining approach (i.e., manually tracing across the full image width with a pointer device such as a mouse or stylus). It is understood that various combinations of the aforementioned editing approaches can be implemented in a graphical user interface so that the expert user can apply the editing tools as most appropriate to the workflow.

In a further embodiment of the manual segmentation editing techniques described above, methods are disclosed for automatically propagating manually corrected edits to adjacent B-scans. Such automated propagation of 2D segmentation results to adjacent scans can substantially reduce the amount of interactive segmentation correction to be performed by an expert user. In a further embodiment, interpolation schemes can also be used to propagate segmentation results across B-scans. In such an interpolation-based approach, a set of non-contiguous B-scans in an OCT image stack can be segmented using the aforementioned automated, semi-automated, and manual methods (e.g., every twentieth B-scan processed interactively). Retinal layer boundaries for the intervening, unsegmented B-scans are then calculated using an appropriate interpolation method (e.g., linear interpolation, cubic spline, B-spline, nearest neighbor, etc.). These intervening retinal layers can be further reviewed by the user for goodness of fit and edited as needed. The combined interpolation and manual editing and propagation methods can be combined in a workflow that allows the user to quickly batch process large OCT datasets comprised of a large number of B-scans while maintaining a high quality segmentation result.

Once segmented, the delineated layer boundaries can be used to define the upper and lower boundaries of an encompassed region of tissue. Such a bounded region, inclusive of the layer boundaries, is herein referred to as a "slab." In the case of a single B-scan, the upper and lower slab boundaries are understood to enclose (or sandwich) a set of pixels (i.e., a 2D slab), while in the case of multiple B-scans the bounding surfaces enclose (or sandwich) a set of voxels (i.e., a 3D slab).

In an embodiment of the methods described herein, structural OCT and OCT angiography data can be combined and presented in a graphical format that aids in interpretation of the combined or composite data. As an example, structural data can be presented in grayscale with angiography data superimposed and rendered in a color scheme to highlight its location within the structural space. Further, angiography data can be color encoded based on the retinal layer slab in which it resides, thereby presenting the user with a visual correlation between blood flow and retina anatomical structure. Such graphical presentations can be generated for both 2D and 3D images.

An aspect of the disclosed methods is that 3D slabs containing OCT angiography data can be compressed to 2D and presented as en face maximum projection angiograms, analogous to clinical images obtained by FA. Further, multiple slabs with differently color coded angiographic data can be presented within a single 2D en face maximum projection angiogram such that depth information for vascular structures is conveyed within the presented 2D angiogram.

Segmented retinal layer slabs can also be used to remove shadowgraphic projection artifacts that are cast anteriorly-to-posteriorly through the dataset during acquisition. In an embodiment, an angiogram of the inner retina can be subtracted from an angiogram of the outer retina (which is avascular in the healthy eye) to remove shadowgraphic artifacts cast from the inner retina to the outer retina. Flow detected in the outer retina after such a subtraction of projection artifact would indicate a retinal pathology, for example, choroidal neovascularization.

In an embodiment, segmented slabs can be used to calculate anatomical thickness maps. These maps can be calculated for individual layers of the retina or across multiple layers of the retina, as specified by the user. Color encoded maps can be generated and presented to aid in the identification of areas of localized thinning, thickening, bulging, or other features.

The above Background and Summary sections are provided to introduce a selection of concepts in simplified form that are further described below in the Detailed Description. The Background and Summary are not intended to identify key features or essential features of the disclosed subject matter, nor are they intended to be used to limit the scope of the disclosed subject matter. Furthermore, the disclosed subject matter is not limited to implementations that solve any or all disadvantages noted in any part of this disclosure.

The superficial inner retinal angiogram shows healthy retinal circulation with a small foveal avascular zone. (D) The deep inner retina angiogram shows the deep retinal plexus which is a network of fine vessels. (E) The healthy outer retinal slab should be absent of flow, but exhibits flow projection artifacts from the inner retina. (F) The choriocapillaris angiogram. (G) The outer retinal angiogram after projection removal (image E minus image C). (H) Inner retinal angiogram. (I) Retinal thickness map segmented from vitreous/ILM to RPE/BM. (J) Composite structural and angiogram B-scan images generated after removal of shadow-graphic projection. (K) Composite C-scan images generated by the flattening of OCT structural and angiogram data volume using RPE/BM.

Figure 2:
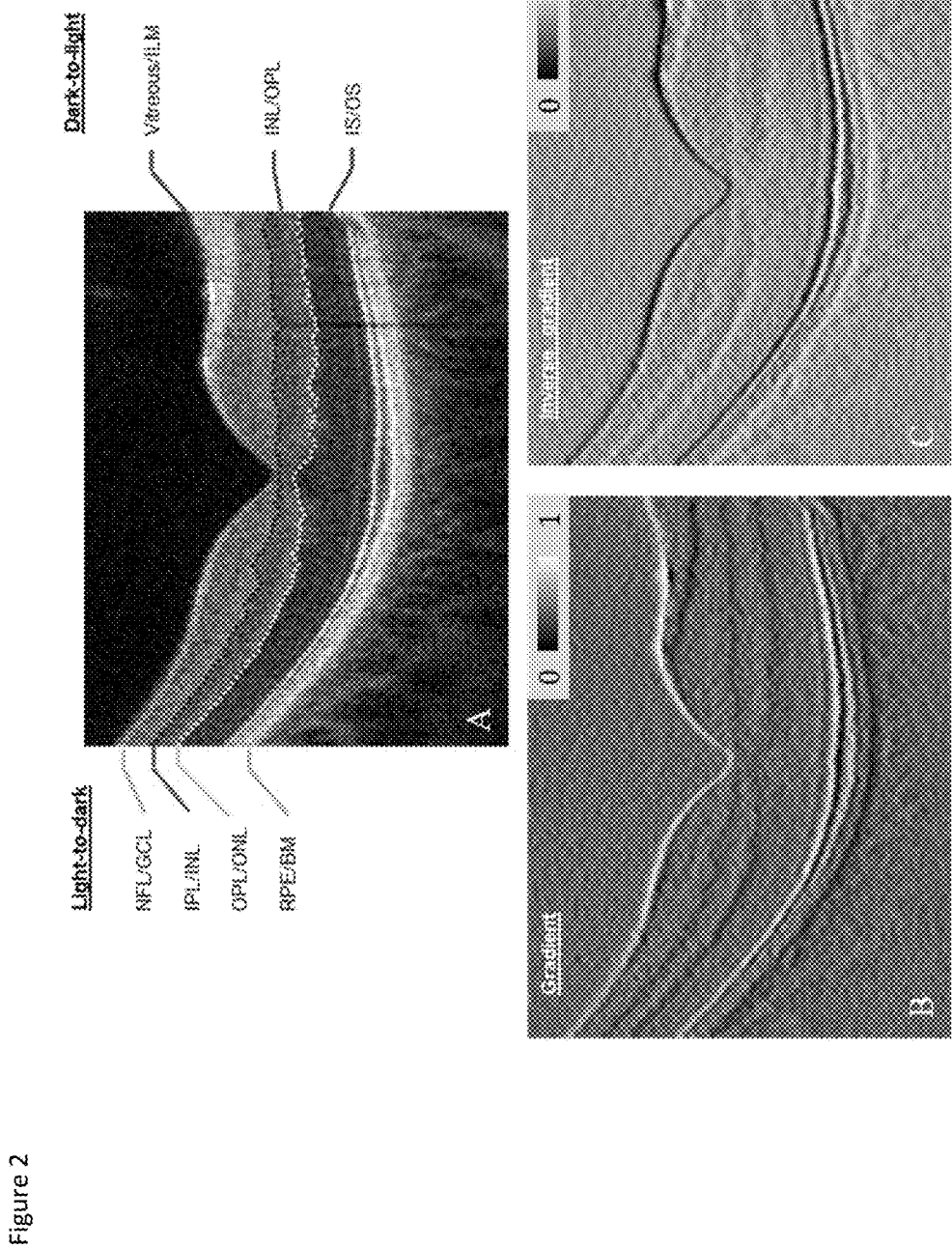

FIG. 2 is a panel of three images showing the light to dark intensity transitions between the anatomic layers of the retina as observed on a structural OCT B-scan, along with OCT angiography data overlaid onto the structural B-scan image. (A) Composite OCT B-scan images with color-coded angiography. Angiography data are overlaid onto the structural images to help graders better visualize the OCT angiography images. Angiography data in the inner retina (between Vitreous/ILM and OPL/ONL) is overlaid as purple, outer retina (between OPL/ONL and IS/OS) as yellow, and choroid (below RPE) as red. (B) Gradient image showing light-to-dark intensity transitions. (C) Inverse gradient image showing dark-to-light intensity transitions.

Figure 3:
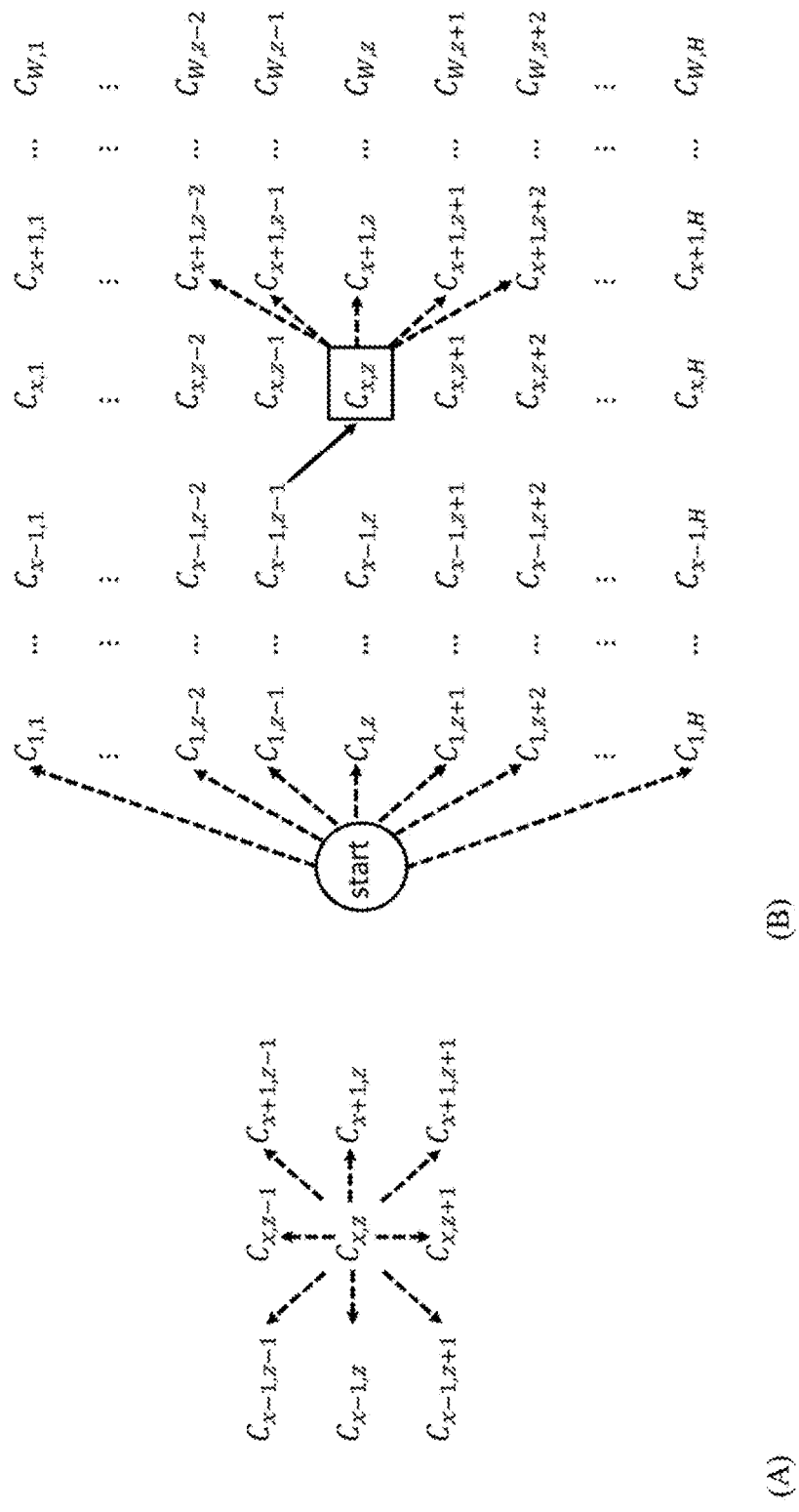

FIG. 3 is a panel of two images showing both a traditional graph search scheme and an exemplary embodiment of a directional graph search scheme. (A) Traditional graph search. (B) Directional graph search where the solid line represents a made move and the dashed lines represent possible next moves. C is the normalized gradient or normalized inverse gradient, x is the B-scan direction having a value between 1 and W, and z is the A-scan direction having a value between 1 and H.

Figure 4:
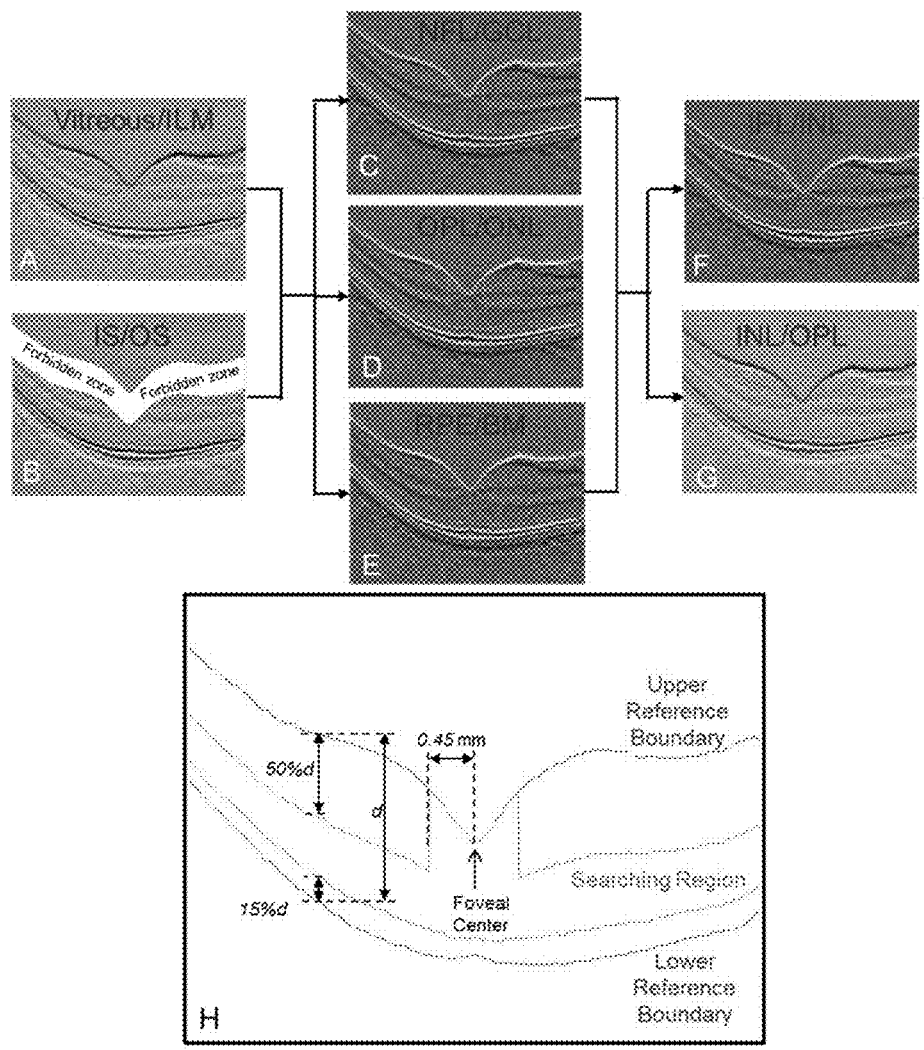

FIG. 4 is a panel of two images, with the upper panel showing a pictorial flowchart of an exemplary three stage layer boundary segmentation work flow, and the lower panel showing exemplary offset parameters (percentages and absolute values) that can be used to define search regions for the segmentation. (A) An inverse gradient image used to segment the vitreous/ILM boundary. (B) Forbidden zone below the segmented vitreous/ILM boundary imposed to guide segmentation IS/OS boundary. (C) Segmented NFL/GCL boundary. (D) Segmented OPL/ONL boundary. (E) Segmented RPE/BM boundary. (F) Segmented IPL/INL boundary. (G) Segmented INL/OPL boundary. (H) Search region parameters for the OPL/ONL boundary.

Figure 5:
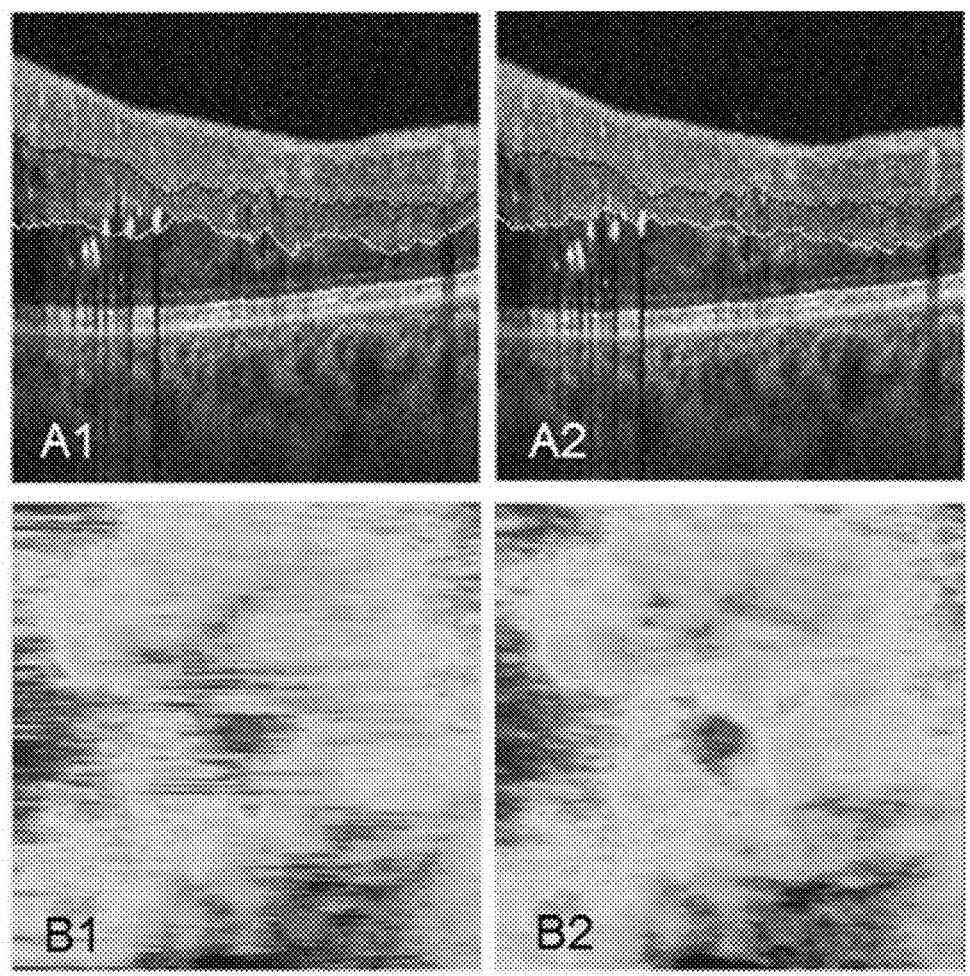

FIG. 5 is a panel of four images showing a comparison of segmentation performance on pathologic tissue using the 2D automated segmentation and propagated 2D automated segmentation approaches described herein. (A1) Red arrow indicates an area where automated segmentation produces an erroneous result due to presence of exudates in the retina. (A2) Red arrow indicates the corrected segmentation recovered by propagated automated segmentation. (B1) En face image map showing the position of the OPL/ONL boundary relative to the bottom of the image for a volumetric set of OCT images having segmentation errors such as that depicted in A1. (B2) En face image map showing the position of the OPL/ONL boundary relative to the bottom of the image for a volumetric set of OCT images after correction of segmentation errors by propagated automated segmentation such as that depicted in A2.

Figure 6:
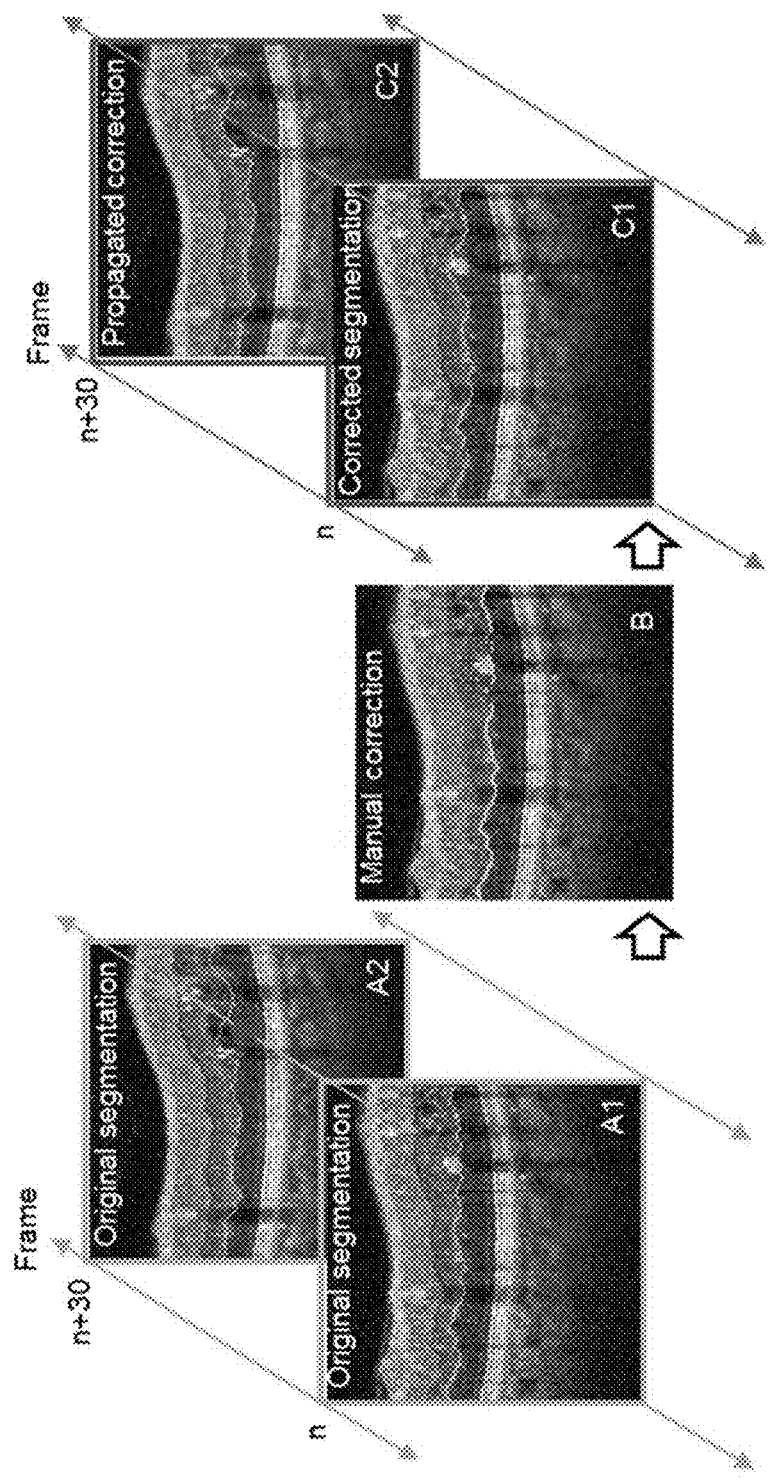

FIG. 6 is a sequence of images showing an example of 2D automated segmentation with and without intelligent manual correction. (A1) Original 2D automated segmentation containing an error in frame n due to an exudate. (A2) The segmentation error from frame n is propagated to frame n+30. (B) Manual correction (denoted by red crosses) performed on frame n. (C1) Results of manual correction to frame n. (C2) Correction propagated to frame n+30. Red arrows identify the segmentation differences in frame n+30 before and after manual correction plus propagation.

Figure 7:
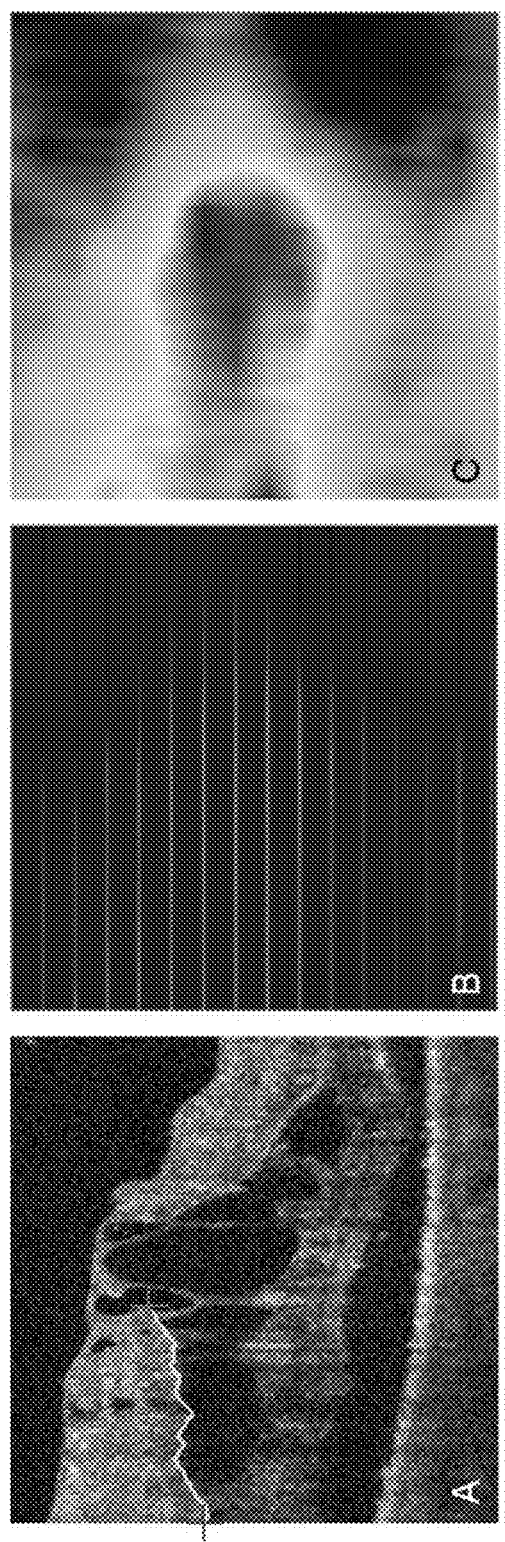

FIG. 7 is a panel of three images showing an example of an editing workflow using intelligent scissors segmentation applied to specified B-scan intervals of the OCT dataset and then interpolated across the entire B-scan volume. (A) Interactive manual segmentation with intelligent scissors, showing a live segmentation of OPL/ONL wherein a mouse click at the red cross sets a start point and repositioning of the mouse pointer to the green cross location displays the results of a directional graph search in real time. (B) En face depth map with segmentation performed every 20 frames. (C) En face depth map after interpolation of (B).

Figure 8:
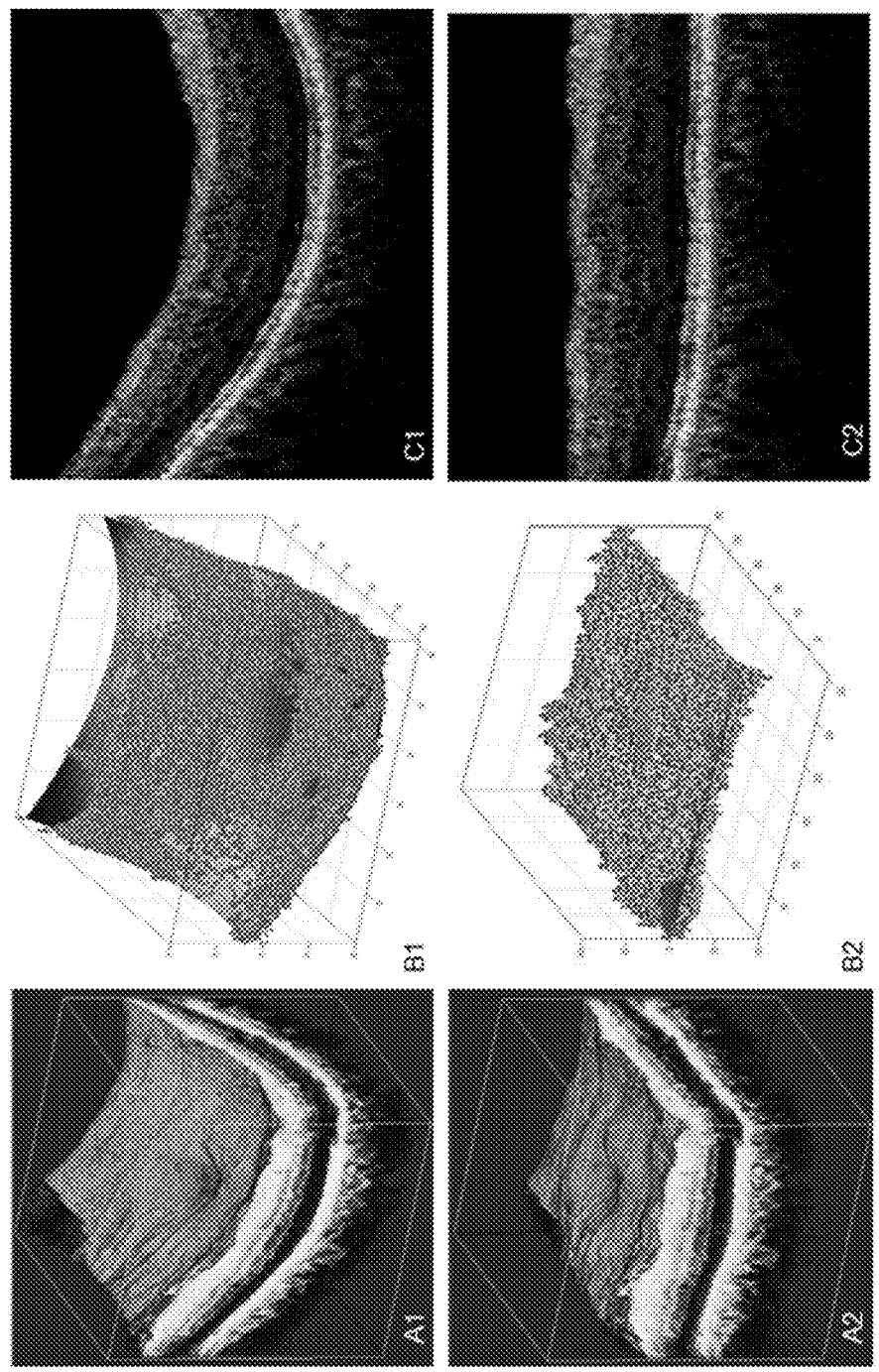

FIG. 8 is a panel of six images showing an exemplary flattening procedure to prepare highly curved 3D datasets for layer segmentation. These images are derived from a 6×6×2 mm OCT retinal volume dataset. (A1) A rendering of the of the original dataset. (A2) A rendering of the flattened configuration of the dataset. (B1) A curved plane fit to the center of mass of each A-scan of the original data set. Each blue dot represents an A-scan center of mass, and the fit plane is color coded by depth location, which provides an estimate of the retinal shape. (B2) A curved plane fit to the center of mass of each A-scan after flattening of the dataset. Each blue dot represents an A-scan center of mass, and the fit plane is color coded by depth location. (C1) A B-scan selected from the original dataset with the center of mass of each A-scan color-coded in blue. (C2) A B-scan selected from the flattened dataset with the center of mass of each A-scan color-coded in blue.

Figure 9:
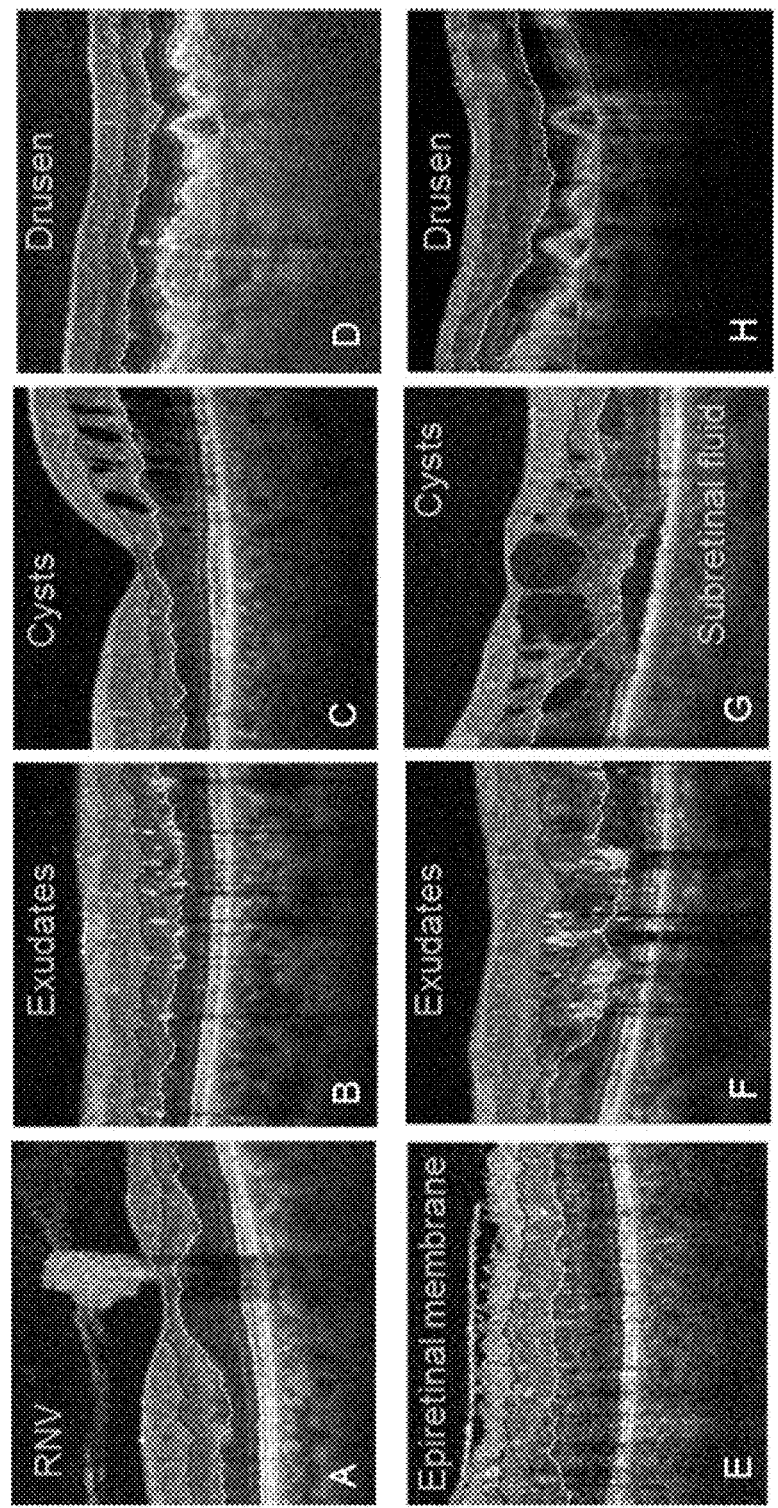

FIG. 9 is a panel of 8 images showing examples of pathological cases where automated segmentation was accurate (upper row), and examples of severe pathology cases where the automated segmentation contained errors (lower row). The pathological cases depicted are as follows: (A) Retinal neovascularization. (B) Exudates. (C) Small intraretinal cysts. (D) Drusen with strong boundary. (E) Epiretinal membrane. (F) Large exudates. (G) Subretinal fluid and large intraretinal cysts. (H) Drusen with weak boundary intensity.

Figure 10:
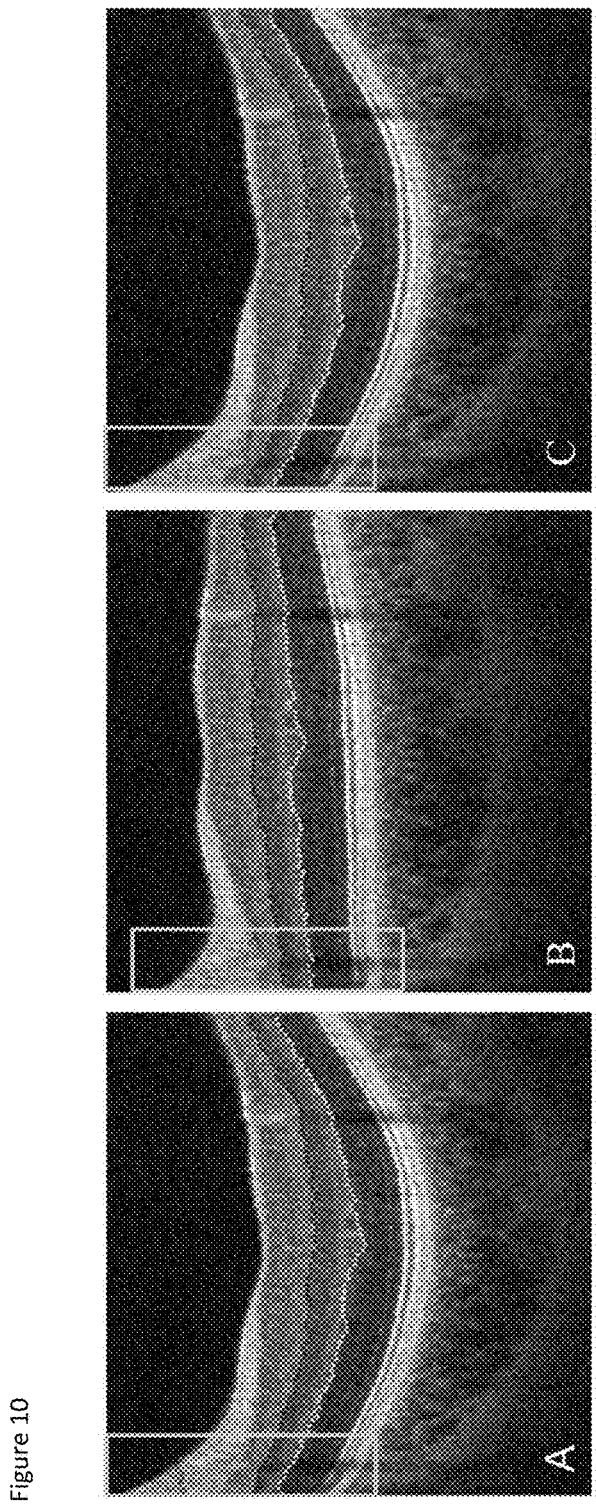
Figure 11:
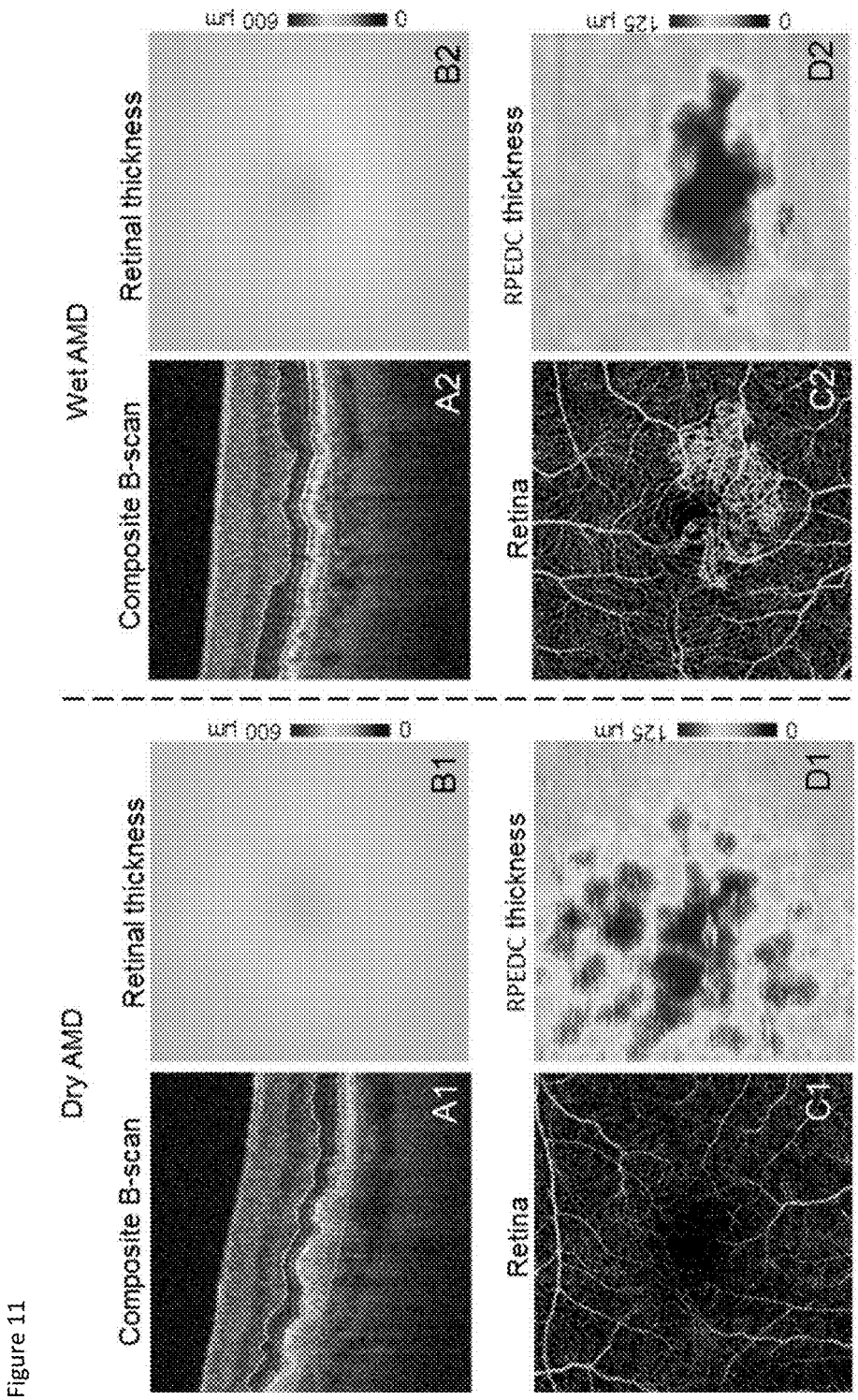

FIG. 10 is a panel of three images showing an example of the use of volume flattening to pre-process an OCT dataset into a more desirable configuration for automated segmentation. (A) Segmentation failure in a 6×6 mm image with stark curvature. Note the segme FIG. 11 is a panel of eight images showing examples of dry AMD and wet AMD cases. (A1) Composite B-scan of a dry AMD case. (B1) Retinal thickness map of a dry AMD case. (C1) Composite en face angiogram of the inner retina (purple) in a dry AMD case. (D1) RPEDC thickness (distance between IS/OS and RPE/BM) map in a dry AMD case. (A2) Composite B-scan of a wet AMD case. (B2) Retinal thickness map of a wet AMD case. (C2) Composite en face angiograms of inner retina (purple) and outer retina (yellow) in a wet AMD case. (D2) RPEDC thickness map in a wet AMD case.

Figure 12:
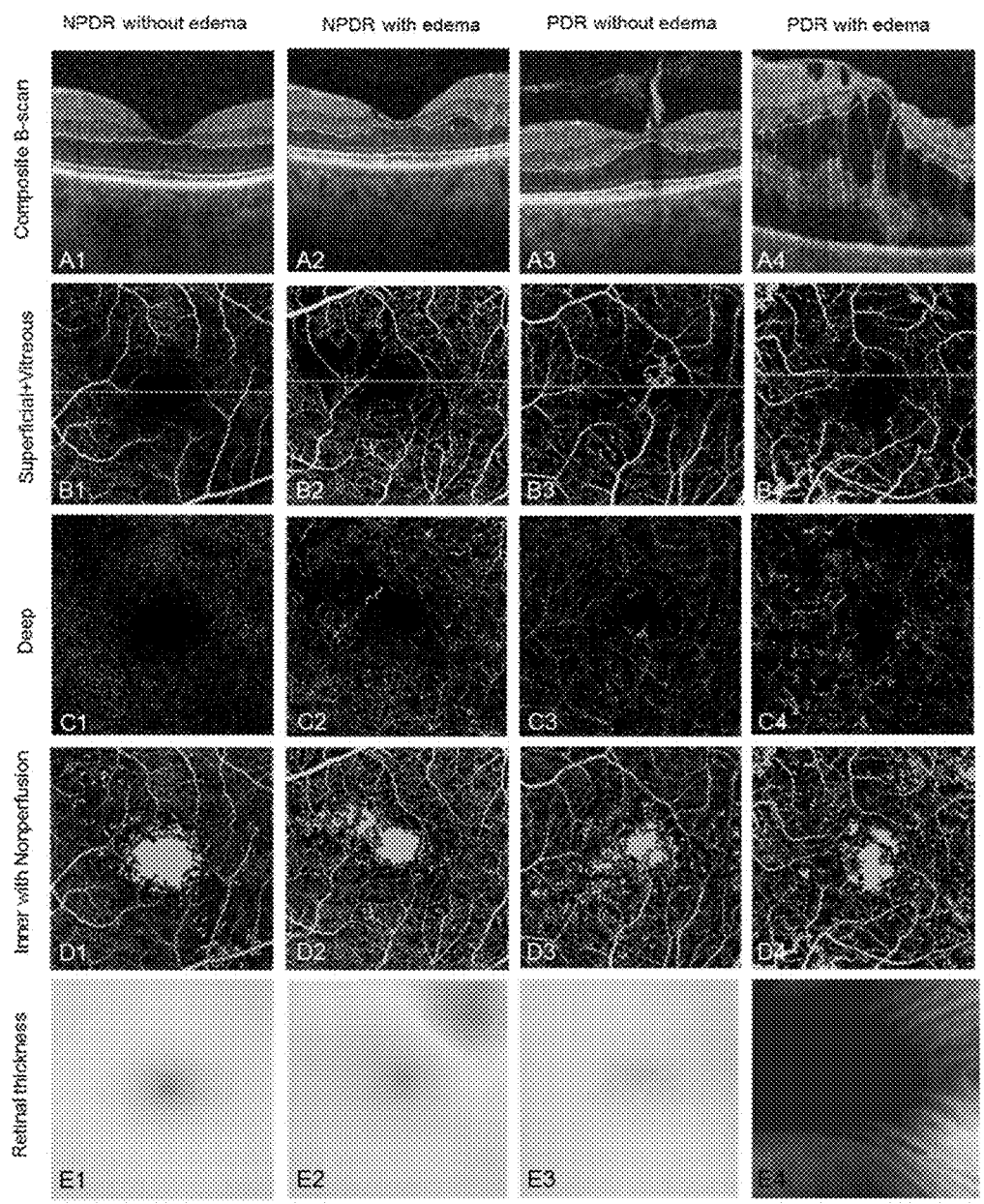

FIG. 12 is a panel of 10 images showing examples of representative results for diabetic retinopathy (DR) cases. (A1, A2, A3, A4) Edema, cyst, extrudes, RNV, and blood flow in different layers can be visualized on the composite B-scan images. (B1, B2, B3, B4) The composite en face angiograms of superficial inner retina and vitreous, where the RNV can be easily seen as pink vessels. The yellow lines in figures B1-B4 mark the position of the corresponding B-scan slices in figures A1-A4. (C1, C2, C3, C4) Angiograms of the deep inner retina. The vascular network is different from the superficial inner retina, although there are projection artifacts from the superficial inner retina. (D1, D2, D3, D4) shows the angiogram of inner retina with nonperfusion areas marked in light blue. The nonperfusion areas are 0.72 mm$^2$, 0.52 mm$^2$, 0.60 mm$^2$, and 0.72 mm$^2$, respectively. (E1, E2, E3, E4) Retinal thickness maps (i.e., the distance from Vitreous/ILM to RPE/BM). The display range of the color map is 0 to 600 μm.

Figure 13:
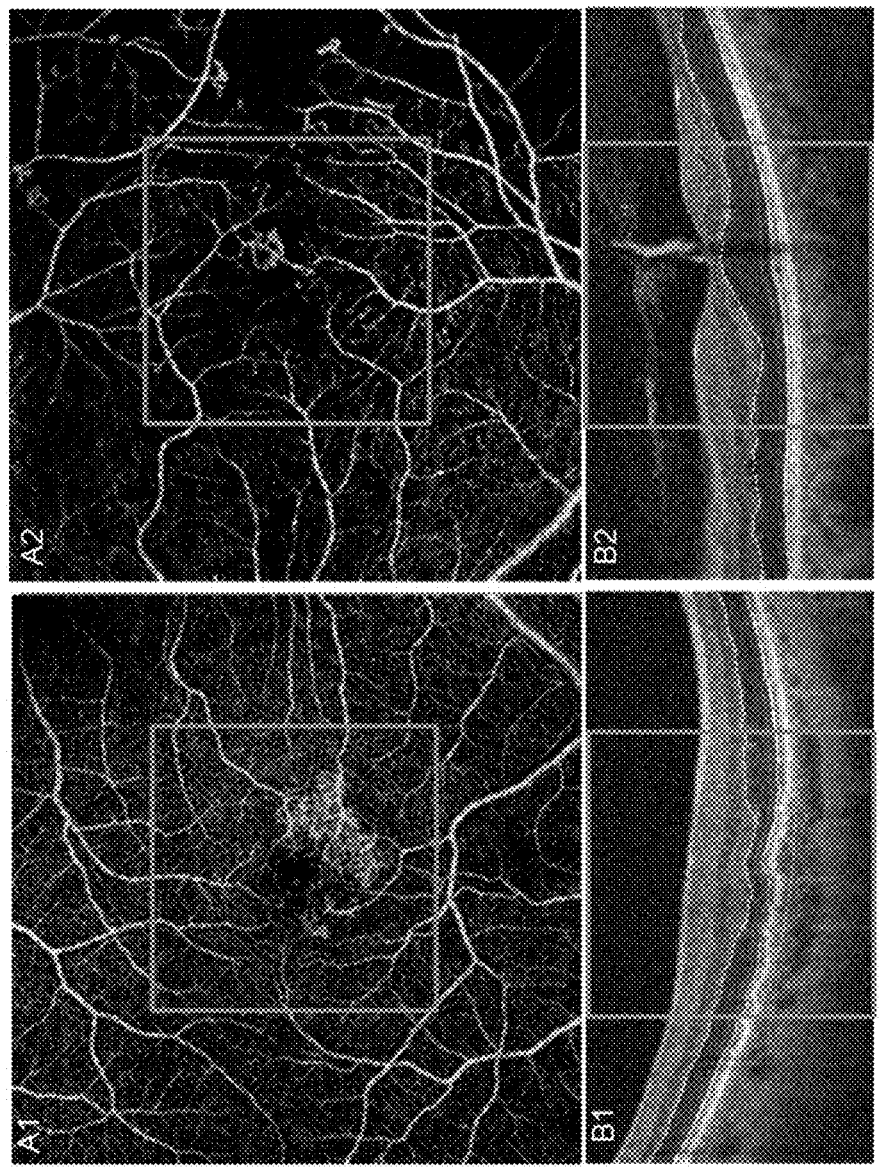

FIG. 13 is a panel of four images showing examples of the disclosed techniques applied to wide-scan OCT images covering a 6×6 mm scan area for cases of diabetic retinopathy. The blue squares mark the 3×3 mm range corresponding to earlier cases in FIGS. 11 and 12. (A1) En face view of the wet AMD case shown in FIG. 11. (A2) En face view of the PDR without edema case shown in FIG. 12. (B1) Composite B-scan of the wet AMD case shown in FIG. 11. (B2) Composite B-scan of the PDR without edema case shown in FIG. 12.

Figure 14:
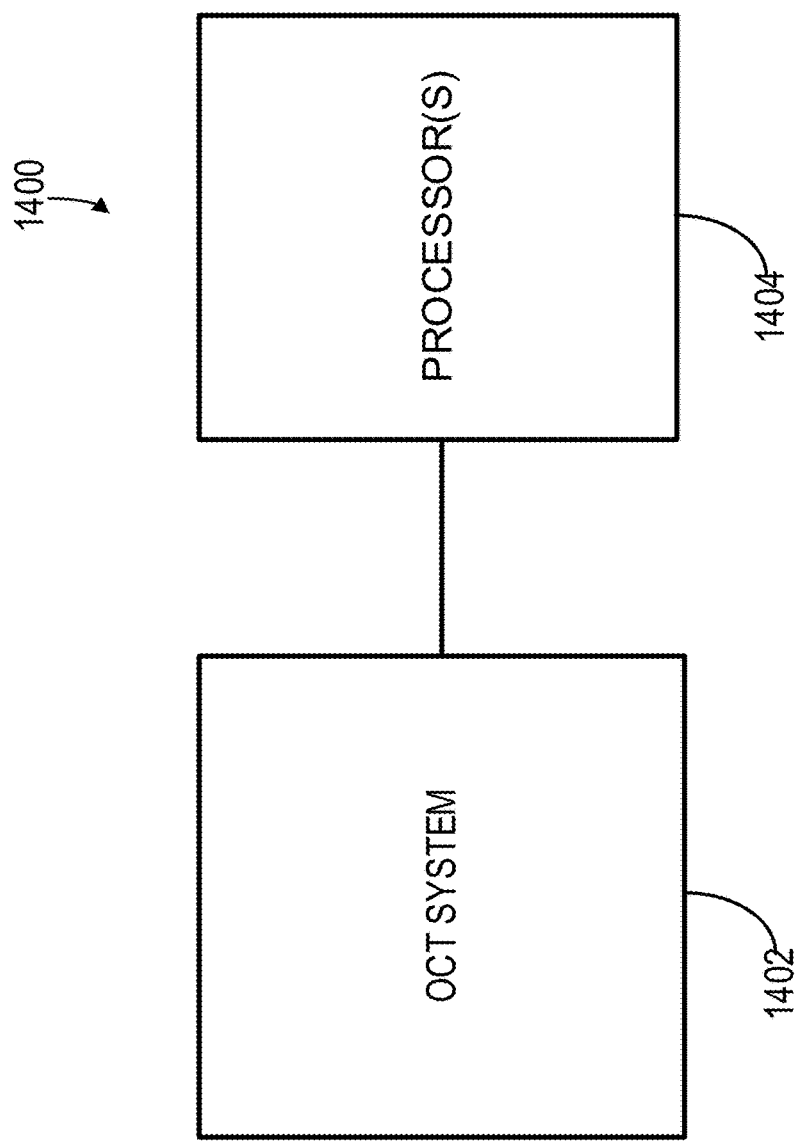

FIG. 14 is a picture that schematically shows an example system for retinal segmentation of OCT imaging and OCT angiography in accordance with the disclosure.

Figure 15:
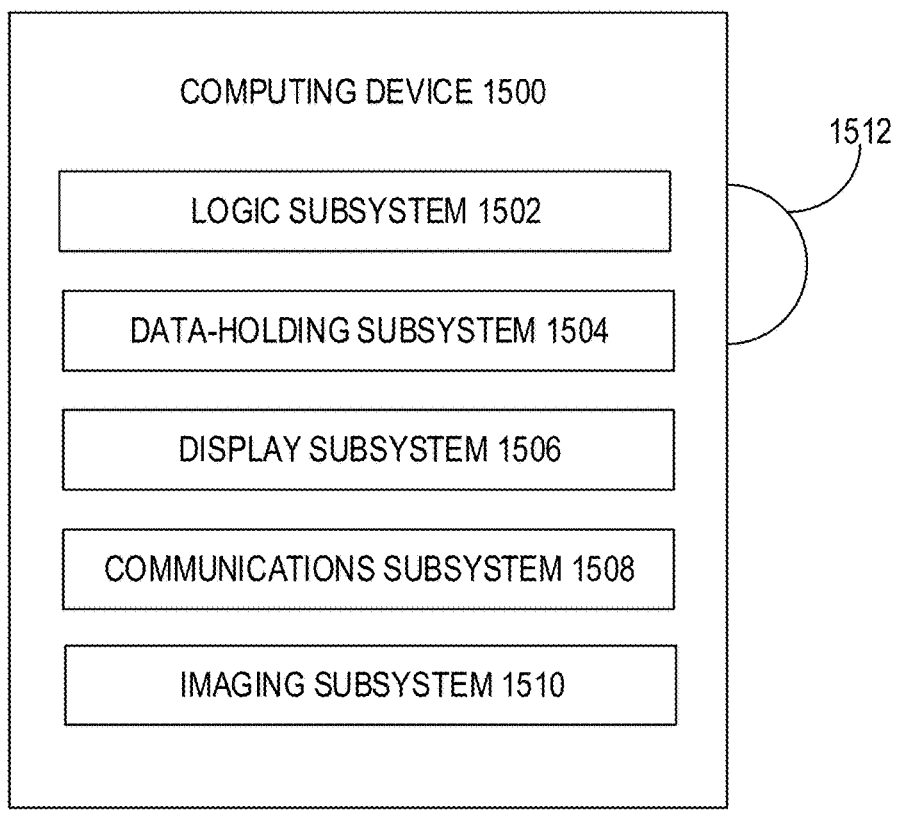

FIG. 15 is a picture that schematically shows an example of a computing system in accordance with the disclosure.

Figure 16:
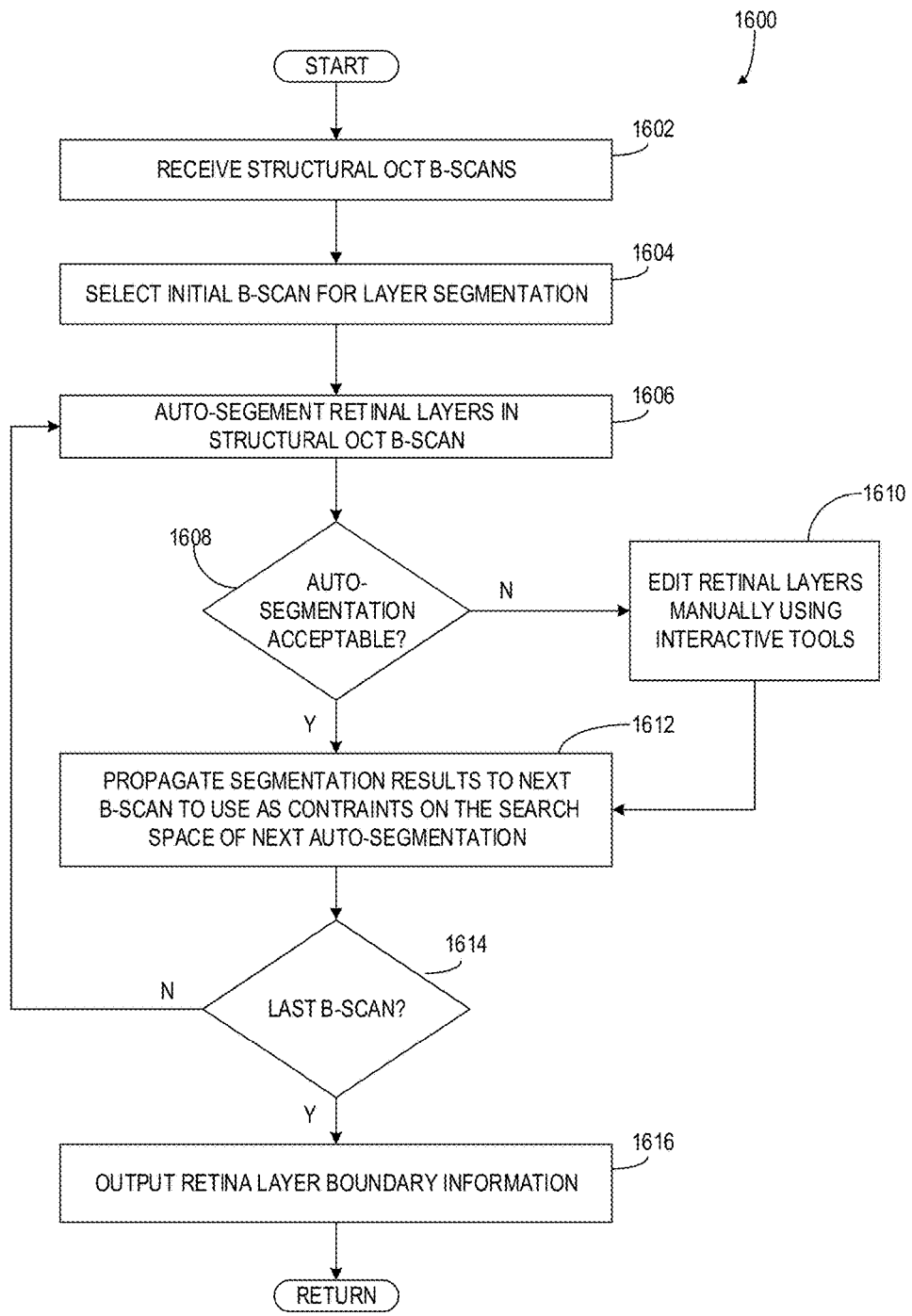

FIG. 16 is a picture of a flowchart showing an example of a method for processing a set of B-scans to segment the layers of the retina in accordance with the disclosure.

Figure 17:
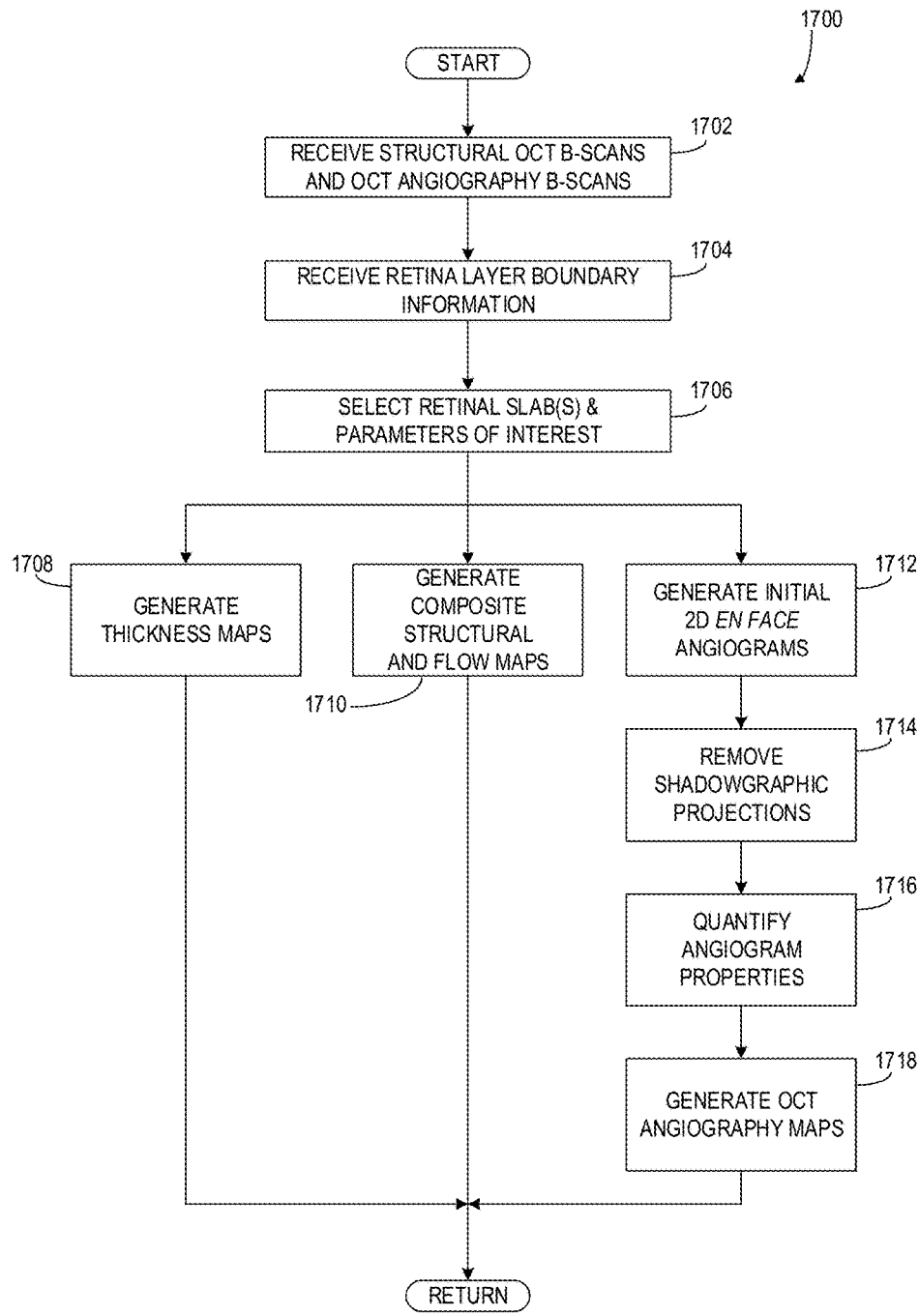

FIG. 17 is a picture of a flowchart showing an example of a method visualize and quantify OCT angiography results using structural OCT B-scans, OCT angiography B-scans, and retina layer segmentation information.

Figure 18:
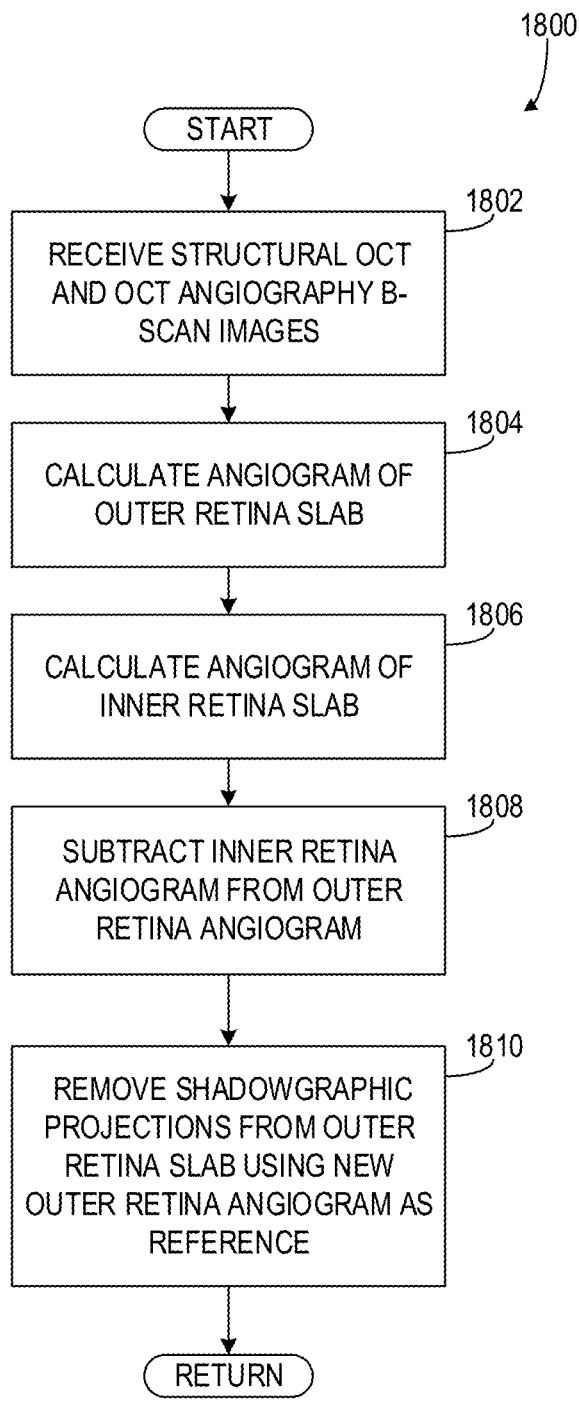

FIG. 18 is a picture of a flowchart showing an example of a method to remove shadowgraphic projection artifacts from OCT angiograms.

DETAILED DESCRIPTION

In the following detailed description, reference is made to the accompanying drawings which form a part hereof, and in which are shown by way of illustration embodiments that can be practiced. It is to be understood that other embodiments can be utilized and structural or logical changes can be made without departing from the scope. Therefore, the following detailed description is not to be taken in a limiting sense, and the scope of embodiments is defined by the appended claims and their equivalents.

Various operations can be described as multiple discrete operations in turn, in a manner that can be helpful in understanding embodiments; however, the order of description should not be construed to imply that these operations are order dependent.

The description can use the terms "embodiment" or "embodiments," which can each refer to one or more of the same or different embodiments. Furthermore, the terms "comprising," "including," "having," and the like, as used with respect to embodiments, are synonymous.

In various embodiments, structure and/or flow information of a sample can be obtained using optical coherence tomography (OCT) (structure) and OCT angiography (structure and flow) imaging based on the detection of spectral interference. Such imaging can be two-dimensional (2-D) or three-dimensional (3-D), depending on the application. Structural imaging can be of an extended depth range relative to prior art methods, and flow imaging can be performed in real time. One or both of structural imaging and flow imaging as disclosed herein can be enlisted for producing 2-D or 3-D images.

Unless otherwise noted or explained, all technical and scientific terms used herein are used according to conventional usage and have the same meaning as commonly understood by one of ordinary skill in the art which the disclosure belongs. Although methods, systems, and apparatuses/materials similar or equivalent to those described herein can be used in the practice or testing of the present disclosure, suitable methods, systems, and apparatuses/materials are described below.

All publications, patent applications, patents, and other references mentioned herein are incorporated by reference in their entirety. In case of conflict, the present specification, including explanation of terms, will control. In addition, the methods, systems, apparatuses, materials, and examples are illustrative only and not intended to be limiting.

In order to facilitate review of the various embodiments of the disclosure, the following explanation of specific terms is provided:

A-scan: A reflectivity profile that contains information about spatial dimensions and location of structures with an item of interest (e.g., an axial depth scan). An A-scan is an axial scan directed along the optical axis of the OCT device and penetrates the sample being imaged. The A-scan encodes reflectivity information (for example, signal intensity) as a function of the depth of the sample being imaged. The A-scan encodes reflectivity information (for example, signal intensity) as a function of depth.

B-scan: A cross-sectional tomograph that can be achieved by laterally combining a series of axial depth scans (e.g., A-scans). A B-scan encodes planar cross-sectional information from the sample and is typically presented as an image. A B-scan encodes planar cross-sectional information from the sample and is typically presented as an image. Thus, a B-scan can be called a cross sectional image.

Dataset: As used herein, a dataset is an ordered-array representation of stored data values that encodes relative spatial location in row-column-depth (x-y-z axes) format. In the context of OCT, as used herein, a dataset can be conceptualized as a three dimensional array of voxels, each voxel having an associated value (for example, an intensity value or a decorrelation value). An A-scan corresponds to a set of collinear voxels along the depth (z-axis) direction of the dataset; a B-scan is made up of set of adjacent A-scans combined in the row or column (x- or y-axis) directions. Such a B-scan can also be referred to as an image, and its constituent voxels referred to as pixels. A collection of adjacent B-scans can be combined form a 3D volumetric set of voxel data referred to as a 3D image. In the system and methods described herein, the dataset obtained by an OCT scanning device is termed a "structural OCT" dataset whose values can, for example, be complex numbers carrying intensity and phase information. This structural OCT dataset can be used to calculate a corresponding dataset termed an "OCT angiography" dataset of decorrelation values reflecting flow within the imaged sample. There is a direct correspondence between the voxels of the structural OCT dataset and the OCT angiography dataset. Thus, values from the datasets can be "overlaid" to present composite images of structure and flow (e.g., tissue microstructure and blood flow) or otherwise combined or compared.

En Face angiogram: OCT angiography data can be presented as a projection of the three dimensional dataset onto a single planar image called an en face angiogram (Wallis J et al, *Med Imaging IEEE Trans* 8, 297-230 (1989); Wang R K et al, 2007 supra; Jia Y et al, 2012 supra); incorporated by reference herein). Construction of such an en face angiogram requires the specification of the upper and lower depth extents that enclose the region of interest within the retina OCT scan to be projected onto the angiogram image. These upper and lower depth extents can be specified as the boundaries between different layers of the retina (e.g., the voxels between the inner limiting membrane and outer plexiform layer can be used to generate a 2D en face angiogram of the inner retina). Once generated, the en face angiogram image can be used to quantify various features of the retinal vasculature as described herein. This quantification typically involves the setting of a threshold value to differentiate, for example, the pixels that represent active vasculature from static tissue within the angiogram. These 2D en face angiograms can be interpreted in a manner similar to traditional angiography techniques such as fluorescein angiography (FA) or indocyanine green (ICG) angiography, and are thus well-suited for clinical use.

Optical coherence tomography (OCT) is an optical signal acquisition and processing method which is capable of capturing micrometer-resolution, three-dimensional images from within optical scattering media, e.g., biological tissue. Optical coherence tomography is based on interferometric techniques and typically employs near-infrared light. The use of relatively long wavelength light allows it to penetrate into the scattering medium. As remarked above, among its many applications, OCT-based ocular imaging has found widespread clinical use and can be performed quickly and easily with minimal expertise. OCT is a non-invasive imaging modality which provides accurate and precise anatomical reproduction of the retinal layers thus is well suited for use in detecting and diagnosing diseases of the retina.

In recent years, OCT techniques have been extended to allow the detection of flow within scattering media, typically using phase-difference, speckle variance, or Doppler variance. Collectively these techniques are termed "OCT angiography" when applied to the detection of blood flow within biological tissues. OCT angiography provides the ability to noninvasively map vasculature and microvascular beds within tissues and characterize blood flow. Applied to the retina, OCT angiography is well suited for visualizing and quantifying the integrity of retinal circulation pathways and for detecting abnormalities in ocular hemodynamics and vascular structure.

The retina is the light sensitive tissue that lines the posterior surface of the eye, bounded on its inner surface by the clear vitreous and on its outer surface by the highly vascularized choroid. Anatomically, the retina is divided into multiple distinct layers composed of different cell and tissue types, with the layers being clearly visible in cross sectional OCT scans of the retina. In the healthy eye, some layers of the retina have associated vascular beds while other layers are avascular. This vascular organization can become disrupted in various pathologic conditions where, for instance, normally vascularized layers can lose capillary support, or normally avascular layers undergo encroachment by pathologic vessel ingrowth. In addition, several pathologies of the eye, including edema, retinal detachment, or drusens, manifest as distortions or disruptions of the retinal layer boundaries themselves. Changes in overall retinal thickness or changes in the thickness of specific layers can also be indicative of ophthalmic pathology.

Because the range of ocular pathologies that impact both the structural and vascular domains of the retina, there is a need for tools to interrogate, quantify, and visualize the retina at the individual layer level. Thus, robust segmentation tools and methods are needed to fully exploit advances in OCT technology. In particular, there is a need for tools to allow the clinician to combine structural OCT imaging data with OCT angiography in a way that elucidates the layer-wise spatial relationship of normal and abnormal features observed in OCT scans of the retina. Accurate segmentation of the retina into its constituent anatomic layers is a prerequisite for such analyses.

Overview of OCT Angiography Image Processing

Segmentation of OCT angiography 3D flow data allows visualization and analysis of isolated vascular beds. OCT structural images provide reference boundaries for the segmentation of 3D OCT angiograms. Useful reference boundaries within the retina (FIG. 1) include, but are not limited to, the inner limiting membrane (ILM), outer boundary of the inner plexiform layer (IPL), inner nuclear layer (INL), outer boundary of the outer plexiform layer (OPL), outer nuclear layer (ONL), retinal pigment epithelium (RPE), and Bruch's membrane (BM). These retina layer boundaries can be automatically segmented in B-scan images using a technique based on graph search methods [20, 21], and edits can be applied to the resultant segmentation during a review process as required. These automated segmentation and editing techniques are described in detail below.

The multiplicity of retina layer boundaries obtained by segmentation across a set of B-scans defines a set of bounding surfaces in three dimensions that separate anatomic layers within the retina. Two separate bounding surfaces can be selected to form the upper and lower boundaries of a volumetric collection of voxels contained (or sandwiched) therein. The term "slab" is used herein to refer to such a volumetric collection of voxels. In the 2D case where the bounding surfaces are defined for a single B-scan, it is understood that the bounded region is comprised of pixels and the "slab" terminology is retained. Slabs of vascular layers within the retina can be identified by specifying two relevant layer boundaries that sandwich them. For example, retinal circulation lies between the ILM and OPL retinal layer boundaries.

It should be noted that the bounding surfaces of a slab need not be from anatomically adjacent layers in the retina; rather, a slab can be defined such that it encompasses one or more anatomical layers of the retina. Furthermore, the bounding surface of a slab need not correspond strictly to an anatomic layer boundary, but can instead be specified as any surface passing through a volumetric OCT scan. As an example, a slab encompassing only vitreous voxels can be defined as the collection of voxels bounded on one side by the inner limiting membrane surface and on the other side by the voxels corresponding to zero-depth level of the A-scans of the 3D data set. Alternately, a slab encompassing only vitreous voxels could be defined as the collection of voxels bounded on one side by the inner limiting membrane surface and on the other side by a surface offset from the inner limiting membrane by a prescribed distance.

When disease pathology disrupts normal tissue anatomy, manual correction of segmentation results is required. In the disclosed method, a directional graph search technique which requires less computation than previous models is used [22]. Furthermore, manual corrections to a B-scan segmentation are propagated forward and backward across multiple adjacent B-scans, expediting image processing and reducing the operator time required to correct errant segmentations.

Figure 1:
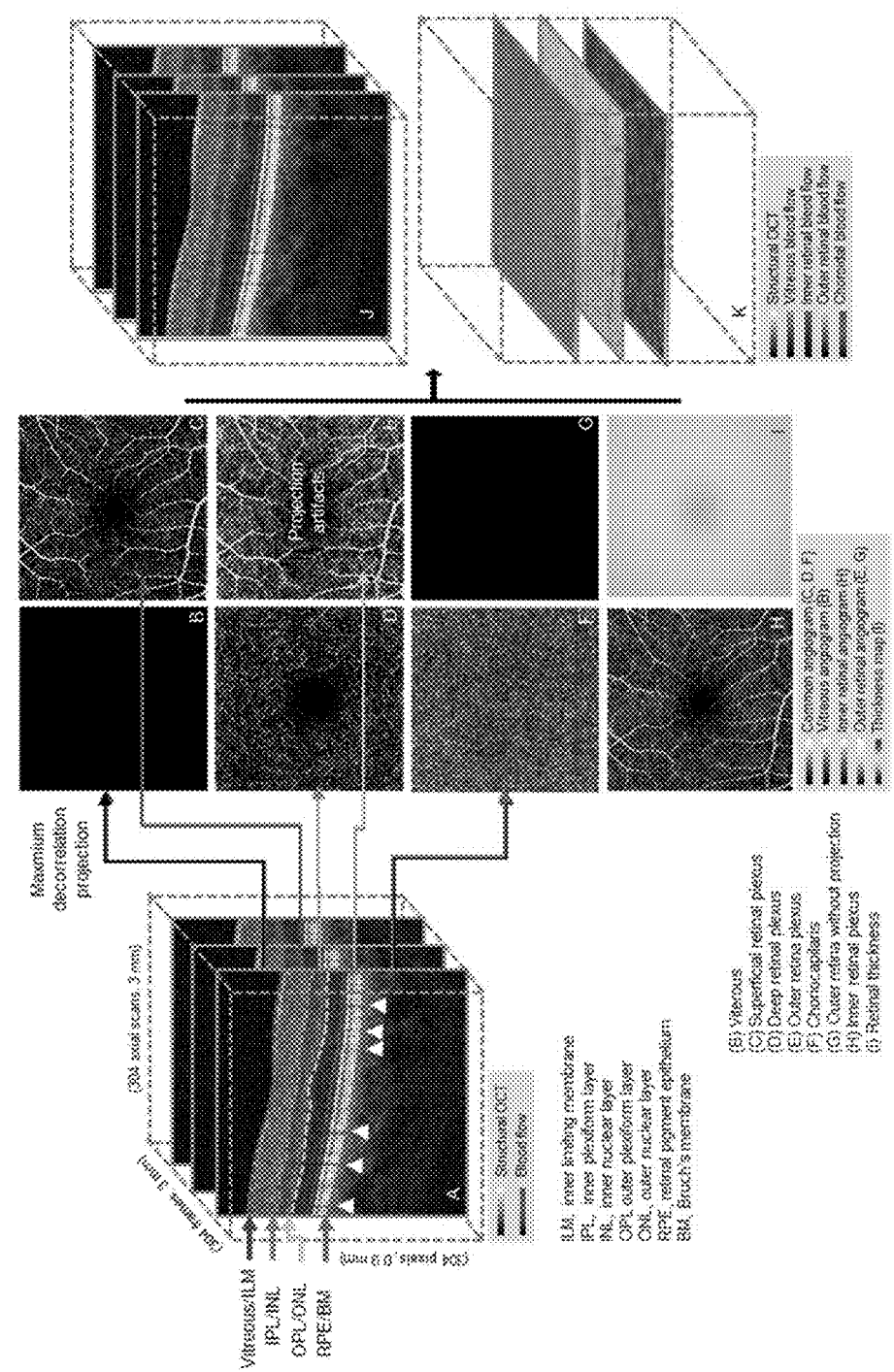
FIG. 1 a set of images showing an overview of the OCT angiography image processing methods for a healthy macula. After motion correction, structural B-scans are segmented to delineate different retina layer boundaries and overlay angiography data. Then 3D slabs are collapsed to 2D and for presentation as en face maximum projection angiograms. Finally, shadow-graphic projection artifacts are removed from B-scans and composite C-scans generated by the flattening of OCT and angiogram volumetric data. (A) The 3D OCT data (3×3×0.9 mm), after motion correction with angiography data overlaid on structural information. (B) The vitreous angiogram shows the absence of flow. (C)

FIG. 1 provides an overview of the data presentation and analysis methods that can be performed using the methods disclosed herein. As shown in panel A of FIG. 1, composite cross-sectional OCT images can be created by combining color-coded angiogram B-scans (which contain flow information) superimposed onto gray-scale structural B-scans (which contain tissue anatomical information), thereby presenting both blood flow and retinal structure together. These composite images provide detailed information on the relative depth of the microvasculature network and the retinal layers in which they are present.

OCT angiograms are generated by summarizing the maximum decorrelation within a slab encompassed by relevant anatomic layers [8]. The 3D angiogram slabs are then compressed and presented as 2D en face images so they can be more easily interpreted in a manner similar to traditional angiography techniques. Using the segmentation of the vitreous/ILM, IPL/INL, OPL/ONL, and RPE/BM layer boundaries, distinct slabs can be visualized as shown in FIG. 1, panels B-G.

In a healthy eye, the vitreous is avascular with no blood flow above the vitreous/ILM reference boundary. Therefore, the angiogram of the slab encompassing the vitreous will appear black as seen in FIG. 1, panel B. The superficial inner retinal angiogram (between vitreous/ILM and IPL/INL) for a healthy eye shows a pattern of retinal circulation with a small foveal avascular zone (FIG. 1, panel C). The deep inner retina angiogram (between IPL/INL and OPL/ONL) for a healthy eye shows the deep retinal plexus which is a network of fine vessels (FIG. 1, panel D).

However, blood flow from larger inner retinal vessels casts a fluctuating shadow which induces signal variation in deeper layers. This variation is detected as decorrelation and results in a shadowgraphic flow projection artefact. Signal characteristics alone cannot distinguish this shadowgraphic flow projection from true deep-tissue blood flow, but it can be recognized by its vertical shadow in the cross-sectional OCT angiogram (FIG. 1, panel A). A comparison of FIG. 1, panel E and FIG. 1, panel C reveals shadowgraphic projection and replication of the vascular patterns from superficial slabs into the deeper layers. This is particularly evident in the outer retinal slab, where the retinal pigment epithelium (RPE) is the dominant projection surface for blood flow (FIG. 1, panel E). Subtracting the angiogram of the inner retina from that of outer retina can remove this shadowgraphic artifact, producing an outer retinal angiogram void of flow, as would be expected in a healthy retina (FIG. 1, panel G). Flow detected in the outer retinal angiogram after removal of projection artifact represents a pathologic condition and typically corresponds to choroidal neovascularization [17, 23].

Composite inner and outer retinal angiogram shows inner retinal blood flow as purple and outer retinal flow as yellow (FIG. 1, panel H). The inner retina angiogram (between vitreous/ILM and OPL/ONL) (FIG. 1, panel H), is a combination of two superficial slabs (FIG. 1, panel C and FIG. 1, panel D). The choriocapillaris angiogram (RPE/BM to 15 μm below), shows nearly confluent flow (FIG. 1, panel F). FIG. 1, panel I shows an en face thickness map of the retina, segmented from vitreous/ILM to RPE/BM.

After removal of flow projection, the outer retinal en face angiogram (FIG. 1, panel G) is then used as the reference for removing shadowgraphic flow projection on cross-sectional outer retina. This produces composite B-scan images with color-coded flow corresponding to various slabs, void of vertical shadowgraphic artifacts in outer retina (FIG. 1, panel J compared to FIG. 1, panel A). Composite C-scan images can be generated in a similar manner. Because of the curved geometry of the retina, the volume data is flattened using RPE/BM to produce flat C-scan images (FIG. 1, panel K).

Layer Segmentation by Directional Graph Search

Graph search is a common technique for generalized image segmentation [24-26]. Disclosed herein is a directional graph search technique for retinal layer segmentation that exploits the fact that retinal layer boundaries are primarily horizontal structures on B-scan structural images. Thus, for a given B-scan, an intensity gradient is defined along the depth of A-scan lines, with each pixel assigned a value $G_{x,z}$, where $$G_{x,z}=I_{x,z}-I_{x,z-1} \qquad (1)$$

and $I_{x,z}$ is the intensity of the pixel, and $I_{x,z-1}$ is the intensity of the previous pixel located within the same A-line. This gradient image can be further normalized as follows using the following formula $$C_{x,z}^{(1)} = \frac{G_{x,z} - \min(G)}{\max(G) - \min(G)} \qquad (2)$$

where $C^{(1)}$ is a normalized value between 0 and 1, and min(G) and max(G) are the minimum and maximum G, respectively, for the entire B-scan structural image containing W columns and H rows.

Because retinal tissue boundaries displayed on structural OCT B-scans have two types of intensity transitions (i.e., light-to-dark and dark-to-light), an inverse gradient image is also generated using the function $$C_{x,z}^{(2)}=1-C_{x,z}^{(1)} \qquad (3)$$

FIG. 2 shows an example of a structural OCT B-scan image and its associated gradient and inverse gradient images. Specifically, in FIG. 2, panel A, seven delineated retinal tissue boundaries are shown on a structural OCT B-scan, along with angiography data that is color-coded by layer and overlaid onto the structural B-scan. FIG. 2, panel B shows a gradient image generated according to Equations (1) and (2) where light-to-dark intensity transitions are represented as low $C^{(1)}$ values, shown here with dark lines at the NFL/GCL, IPL/INL, OPL/ONL and RPE/BM tissue boundaries. FIG. 2, panel C shows an inverse gradient image generated according to Equation (3), where dark-to-light intensity transitions are represented as low $C^{(2)}$ values, and appear as horizontal black lines at the vitreous/ILM, IS/OS, and INL/OPL boundaries.

Graph search algorithms segment an image by connecting C values with the lowest overall cost. Typically, a graph search algorithm considers all 8 surrounding neighbors when determining the next optimal connection (FIG. 3, panel A). The directional graph search algorithm described herein considers only 5 directional neighbors, as illustrated by the 5 dashed lines of FIG. 3, panel B. Because retinal layers are nearly flat, it can be assumed tissue layer boundaries will extend laterally across structural OCT B-scans in a continuous fashion, and are unlikely to reverse in direction. Thus, the graph search is performed directionally, from left to right, excluding from the search space the left side neighbors and the upward $C_{x,z-1}$ and downward $C_{x,z+1}$ neighbors. To make the directional graph search sensitive to stark boundary changes, both the $C_{x+1,z-2}$ and $C_{x+1,z+2}$ positions are include in the search space. A weight of 1 is assigned to $C_{x+1,z-1}$, $C_{x,+1,z}$, and $C_{x+1,z+1}$ neighbors, and a weight of 1.4 to $C_{x,z-2}$ and $C_{x,z+2}$ neighbors, thus increasing the extra cost of steeper paths.

In order to automatically detect the start point of a retinal layer boundary, the directional graph search starts from a virtual start point located outside the graph, such that all adjacent neighbors are in the first column (FIG. 3, panel B). The lowest cost of connecting C values then proceeds rightward in a column-wise manner and ends at the rightmost column. This directional graph search method reduces computation complexity since fewer neighbors are considered at each step across the B-scan, thereby improving segmentation efficiency.

Automated Segmentation of Seven Retinal Boundaries

Automated image segmentation of retinal layers is a common practice in image processing and has been described at length in the literature [20, 21, 27-29]. Similar to previous demonstrations [19, 21], the directional graph search disclosed herein is configured to detect up to seven boundaries of interest on a B-scan image depicting a cross section through the retina (as in FIG. 2, panel A). In an embodiment of the segmentation method, seven boundaries are delineated in three stages in the order shown in the flow diagram at the top of FIG. 4, corresponding to the images of FIG. 4, panels A, panel B, panel C, panel D, panel E, panel F, and panel G. At stage 1, the inverse gradient image is used to segment either vitreous/ILM (FIG. 4, panel A) or IS/OS (FIG. 4, panel B), using the function $C^{(2)}$. After segmentation of either the vitreous/ILM or IS/OS, a cost value of 1 is assigned to pixels at a specified distance (for example, 60 μm) below and above that layer boundary, respectively. This assignment imposes a so-called "forbidden zone" about the detected boundary, such that the subsequent search for the next boundary will not pass through the forbidden zone pixels. Assignment of such forbidden zone cost values effectively imposes a buffer zone in the proximity of the detected layer boundary and ensures that high cost pixels will not be captured in the subsequent automated layer segmentation. An example of such a forbidden zone is shown in FIG. 4, panel B, where the vitreous/ILM boundary has been detected and the forbidden zone about that boundary is imposed prior to segmentation IS/OS boundary.

At stage 2, directional graph search is performed on the gradient image $C^{(1)}$ to segment three more tissue boundaries: the NFL/GCL (FIG. 4, panel C), OPL/ONL (FIG. 4, panel D), and RPE/BM (FIG. 4, panel E). The vitreous/ILM and IS/OS boundaries identified in stage 1 are used to establish an upper reference boundary (URB) and lower reference boundary (LRB), respectively so that relative distances from these references can be defined. For each A-scan a distance, d, between the URB and LRB is determined and used to define search regions for within which to search for the three tissue boundaries specified above. These search regions are defined as relative or absolute offsets from the URB and LRB. Relative offsets are expressed as fractional amounts of the d value for each A-scan. Examples of percentages and absolute values to be used for these offsets are presented in Table 1. For example, FIG. 4, panel H shows the search region for the OPL/ONL boundary 0.45 mm left of the fovea is 50%×d below URB and 15%×d above LRB. Similarly, RPE/BM (FIG. 4, panel E) was searched in a region on the gradient image using the parameters in Table 1.

At stage 3, the remaining two boundaries, IPL/INL and INL/OPL, are searched between NFL/GCL (UBR) and OPL/ONL (LBR) using the gradient image $C^{(1)}$ (FIG. 4, panel F) and inverse gradient image $C^{(2)}$ (FIG. 4, panel G), respectively.

The foveal center is detected by evaluating the distance between vitreous/ILM and IS/OS. In a certain B-scan frame, if the difference between the largest and smallest distances is greater than 60 μm, the column with smallest distance is set as the center of the fovea. Different parameters for calculating the search range are used for left of the foveal center, near the foveal center, and to the right of the foveal center, as shown in Table 1 The processing time for segmenting the 7 layers on a 304×512 pixel image as depicted in FIG. 4 was 330 ms using an Intel® Xeon® E3-1226 computer@3.30 GHz with programming implemented in the Matlab environment.

TABLE 1

Parameters for setting searching range.

|  | URB[1] | LRB[2] | Left of fovea[3] | | Foveal center[4] | | Right of fovea[5] | |
| --- | --- | --- | --- | --- | --- | --- | --- | --- |
|  |  |  | Ratio to URB | Ratio to LRB | Ratio to URB | Ratio to LRB | Ratio to URB | Ratio to LRB |
| NFL/GCL | Vitreous/ILM | IS/OS | 0% | 80% | 0% | 95% | 0% | 40%[6] |
| OPL/ONL | Vitreous/ILM | IS/OS | 50% | 15% | 0% | 15% | 50% | 15% |
| RPE/BM | IS/OS | 100 μm below IS/OS | 20% | 5% | 20% | 5% | 20% | 5% |
| IPL/INL | NFL/GCL | OPL/ONL | 10% | 20% | 0% | 20% | 10% | 20% |
| INL/OPL | NFL/GCL | OPL/ONL | 30% | 5% | 0% | 5% | 30% | 5% |

This set of parameters is for segmenting OD (right eye) 6 × 6 mm. Switch the parameters of Left of fovea and Right of fovea for OS (left eye).
[1]URB, upper reference boundary.
[2]LRB, lower reference boundary.
[3]0.45 mm left from fovea center.
[4]0.45 mm around fovea center.
[5]0.45 mm right from fovea center.
[6]70% for 3 × 3 mm scan.

Layer Segmentation in Diseased Eye

Propagated 2D Automated Segmentation

In the clinic, OCT images often contain pathological abnormalities such as cysts, exudates, drusen, and/or layer separation. These abnormalities are difficult to account for on conventional 2D and 3D segmentation algorithms [20, 29]. As a result, these pathologic features can introduce segmentation errors when applied to B-scans. To mitigate these errors, a method to propagate 2D segmentation results to adjacent B-scans is implemented so that "prior information" can guide the segmentation process. The method assumes that the boundaries won't change substantially in adjacent B-scan frames, so segmentation results from previous B-scans are used to inform the search regions for the B-scan undergoing segmentation. This propagated automated segmentation approach is initialized by segmenting a B-scan frame with relatively few pathological structures. To segment the remaining B-scan frames, aside from calculating the search region according to Table 1, the search region for a particular boundary is further confined to 15 µm above and below the boundary in previous segmented B-scan frame. In this manner, the segmentation is propagated to the rest of the volume B-scan by B-scan. FIG. 5, panel A1 shows an example of layer segmentation errantly attracted to strong reflectors, exudates in this case. FIG. 5, panel A2 shows the improved segmentation recovered by propagated automated segmentation.

The en face images in FIG. 5, panel B1 and FIG. 5, panel B2 map the distance between the segmented OPL/ONL position and the bottom of the image, with each horizontal line corresponding to a B-scan frame. The conventional 2D algorithm (FIG. 5, panel B1) shows segmentation errors, while an accurate segmentation from propagated 2D algorithm generates a continuous map (FIG. 5, panel B2). This map of boundary curve position facilitates monitoring and identification the possible segmentation error.

Propagated 2D Automated Segmentation with Intelligent Manual Correction

When propagated 2D automated segmentation fails, expert manual correction can be utilized along with the segmentation methods described herein. FIG. 6 shows an exemplary case where manual correction is incorporated into a propagated automatic segmentation scheme to correct segmentation errors present across multiple B-scan images in a volumetric scan. As shown in this example, a localized exudate region in FIG. 6, panel A1 causes a segmentation error at frame n that is propagated forward through the image stack to frame n+30 at FIG. 6, panel A2 (denoted by a red arrow). In an exemplary manual correction mode, the user pinpoints several landmark positions using a mouse or other pointer device (FIG. 6, panel B, shown as 4 red crosses) to re-route the errant segmentation in the vicinity of the exudate. An optimal path through these landmarks is automatically located using the directed graph search approach described herein. After such manual corrections are made on an individual B-scan within a volume, the corrected boundary curve is propagated to adjacent frames as described above. For example, the manual correction of frame n in FIG. 6, panel B results in the re-routed boundary shown in FIG. 6, panel C1, which is then propagated across successive frames to frame n+30 (i.e., propagated correction), as shown in FIG. 6, panel C2 and identified by the red arrow.

Interactive Manual Segmentation with Intelligent Scissors

For cases where the retina is highly deformed and the automated segmentation completely fails, an interactive manual segmentation method can be employed. One embodiment of manual segmentation incorporates the directed graph search described herein with an intelligent scissors tool [24], such that the manual segmentation is displayed in real time while the user moves the cursor along the boundary path (FIG. 7, panel A).

Interpolation Mode

In an embodiment, automated/manual segmentation can also be applied at regular intervals across the image volume (FIG. 7, panel B and panel C), followed by interpolation across the entire volume in the manner described above. Such an approach greatly reduces the segmentation workload while maintaining reasonable accuracy. The frame interval for manual segmentation is determined according to the variation among B-scan frames. This implementation provides a balance between segmentation accuracy and required manual segmentation workload.

Volume Flattening

On larger images, such as 6×6 mm images, the automated segmentation using directional graph search can fail in a given B-scan due to significant tissue curvature of the retina geometry (FIG. 10, panel A, inside the yellow box). To address this problem a flattening procedure (illustrated in FIG. 8) was developed to process highly curved retina structures into a flatter configuration more amenable to the directional graph search method described herein. FIG. 8 panel A1 and panel A2 show volume renderings of an original, highly curved OCT dataset and its corresponding flattened OCT dataset, respectively. In one embodiment, the flattening procedure first finds the center of mass (pixel intensity) of each A-scan, represented as blue dots in FIG. 8, panel B1 and panel C1. A curved plane is fitted to these centers of mass and a shift imposed along the depth (z) direction to transform the plane and volumetric data, into a flat plane (FIG. 8, panel B2 and panel C2) and a flattened retinal volume, respectively. By using the center of mass instead of an anatomic tissue plane, the volume flattening procedure is not subject to boundary distortion caused by pathology.

EXAMPLES

The following examples are illustrative of the disclosed method. In light of this disclosure, those skilled in the art will recognize that variations of these examples and other examples of the disclosed method would be possible without undue experimentation.

OCT Angiography Data Acquisition

The OCT angiography data was acquired using a commercial spectral domain OCT instrument (RTVue-XR; Optovue). It has a center wavelength of 840 nm with a full-width half-maximum bandwidth of 45 nm and an axial scan rate of 70 kHz. Volumetric macular scans consisted of a 3×3 mm or 6×6 mm area with a 1.6 mm depth (304×304× 512 pixels). In the fast transverse scanning direction, 304 A-scans were sampled. Two repeated B-scans were captured at a fixed position before proceeding to the next location. A total of 304 locations along a 3 mm or 6 mm distance in the slow transverse direction were sampled to form a 3D data cube. The split spectrum amplitude decorrelation angiography (SSADA) algorithm detected blood flow by calculating the signal amplitude-decorrelation between two consecutive B-scans of the same location. All 608 B-scans in each data cube were acquired in 2.9 seconds. Two volumetric raster scans, including one x-fast scan and one y-fast scan, were obtained and registered [30].

Study Population

A systematic test of the directed graph segmentation technique was performed on eyes with DR and AMD. In the DR study, 5 normal cases, 10 non-proliferative DR (NPDR), and 10 proliferative DR (PDR) were studied. The layers of interest for segmentation included vitreous/ILM, IPL/INL, OPL/ONL, RPE/BM. In the AMD study, 4 normal, 4 dry AMD and 4 wet AMD eyes were examined. The layers of interest for segmentation included vitreous/ILM, OPL/ONL, IS/OS, RPE/BM. Table 2 summarizes the average number of layers corrected and the processing time required.

Layer Segmentation Performance
Automated Segmentation of Pathology

FIG. 9 shows that the 2D automated algorithm correctly segmented the tissue boundaries despite disruption caused from retinal neovascularization (RNV) (FIG. 9, panel A), small exudates (FIG. 9, panel B), small intraretinal cysts (FIG. 9, panel C), or drusen with strong boundary (FIG. 9, panel D). However, the algorithm failed in some severe pathology cases. During segmentation of epiretinal membrane (FIG. 9, panel E), the NFL/GCL boundary was assigned to the epiretinal membrane, causing an upshift in the search region, and therefore incorrect segmentation for IPL/INL, INL/OPL and OPL/ONL. Large exudates (FIG. 9, panel F), distorted the OPL/ONL boundary, and therefore caused incorrect segmentation of NFL/GCL, IPL/INL and INL/OPL. Also, large exudates were shown to cast a shadow artifact extending past the IS/OS boundary. Subretinal fluid and large intraretinal cysts (FIG. 9, panel G) disrupted the IS/OS and OPL/ONL boundary and as result, the NFL/GCL, IPL/INL and INL/OPL were also segmented incorrectly. Drusen with weak boundary intensity (FIG. 9, panel H) caused the segmentation of the IS/OS and RPE to inaccurately follow the more elevated drusens, and as a consequence NFL/GCL, IPL/INL and INL/OPL are also segmented incorrectly. Interpolation mode was used rarely (FIG. 7, PDR with edema).

Segmentation Processing Time and Accuracy

During segmentation, the number of manual corrections made on each type of boundary was recorded for both DR and AMD. The average number of manual corrections is given in Table 2. The automated segmentation of vitreous/ILM was highly accurate in DR and AMD cases. In severe DR cases, edema sometimes caused tissue boundaries to be located outside of the search regions defined in Table 1, and therefore required manual corrections of both the IPL/INL and OPL/ONL boundaries. Similarly, AMD with large drusen caused segmentation failure of OPL/ONL and IS/OS. RPE/BM required manual correction in AMD cases where the boundary became unclear. In general, an increase in severity of either DR or AMD required a larger average processing time. Compared to a purely manual segmentation (typically taking 3-4 h to complete, [22]), the disclosed intelligent manual corrections method efficiently segmented tissue boundaries in eyes with DR and AMD, taking 15 minutes to complete, including the most difficult case.

TABLE 2

Average time for processing different clinical cases

| Case | | # of subjects | Average # of boundaries corrected | | | | Average time (mins) |
|---|---|---|---|---|---|---|---|
| | | | Vitreous/ILM | IPL/INL | OPL/ONL | RPE/BM | |
| DR | Normal | 5 | 0 | 0 | <1 | 0 | 2 |
| | NPDR w/o edema | 5 | 0 | <1 | 2 | 0 | 3 |
| | NPDR w/ edema | 5 | 0 | 3 | 4 | 0 | 5 |
| | PDR w/o edema | 5 | 0 | 2 | 2 | 0 | 3 |
| | PDR w/ edema* | 5 | <1 | 6 | 11 | 0 | 10 |
| | | | Vitreous/ILM | OPL/ONL | IS/OS | RPE/BM | |
| AMD | Normal | 4 | 0 | <1 | 0 | 0 | 2 |
| | Dry AMD | 4 | 0 | 2 | 4 | 2 | 6 |
| | Wet AMD | 4 | 0 | 3 | 13 | 6 | 12 |

*1 case was segmented using the interpolation mode.

TABLE 3

Segmentation accuracy of different clinical cases

| Case | | Mean ± Std (pixels) | | | |
|---|---|---|---|---|---|
| | | Vitreous/ILM | IPL/INL | OPL/ONL | RPE/BM |
| DR | Normal | 0.25 ± 0.08 | 0.97 ± 0.64 | 0.13 ± 0.12 | 0.26 ± 0.09 |
| | NPDR w/o edema | 0.04 ± 0.03 | 0.29 ± 0.30 | 0.13 ± 0.23 | 0.16 ± 0.19 |
| | NPDR w/ edema | 0.04 ± 0.03 | 0.70 ± 0.98 | 2.85 ± 4.05 | 0.14 ± 0.18 |
| | PDR w/o edema | 0.06 ± 0.08 | 0.32 ± 0.50 | 1.60 ± 1.84 | 0.08 ± 0.08 |
| | PDR w/ edema* | 0.25 ± 0.45 | 3.23 ± 1.98 | 5.28 ± 3.72 | 1.37 ± 1.82 |
| | | Vitreous/ILM | OPL/ONL | IS/OS | RPE/BM |
| AMD | Normal | 0.25 ± 0.08 | 0.13 ± 0.12 | 0.21 ± 0.05 | 0.26 ± 0.09 |
| | Dry AMD | 0.02 ± 0.02 | 1.45 ± 2.96 | 0.31 ± 0.57 | 0.51 ± 0.88 |
| | Wet AMD | 0.03 ± 0.03 | 0.97 ± 1.6 | 0.26 ± 0.58 | 0.91 ± 1.02 |

To evaluate the segmentation accuracy, the results of manual segmentation using intelligent scissors was compared to those generated by propagated automated segmentation with manual correction. For each case, 20 B-scan images were randomly selected for evaluation. Three graders independently performed manual segmentation of each tissue boundary. The manually segmented boundaries were averaged among the three graders and taken as gold standard. The absolute errors of the propagated automated segmentation with manual correction was determined (mean±std). The results are given in Table 3. In the majority of images, the segmentation error is less than 1 pixel (3.1 µm).

Volume Flattening

The aforementioned volume flattening procedure was able to solve stark curvature segmentation errors, as demonstrated in the B-scan images of FIG. 10. The yellow box in FIG. 10, panel A demonstrates segmentation failure at multiple tissue boundaries in an area of stark curvature. By flattening the volumetric data, the automated segmentation algorithm was able to accurately segment all seven tissue boundaries inside the yellow box as shown in FIG. 10, panel B. When the image was restored to its original curvature, the corrected segmentation remained as shown in FIG. 10, panel C. This automated volume flattening allows for efficient image processing of large area OCT scans (for example, wide-field scans of 6×6 mm or greater), where stark boundary curvature is more prevalent over the imaged region of interest.

Advanced Image Processing: Diseased Eye

Age Related Macular Degeneration

Choroidal neovascularization is the pathologic feature of wet AMD. The disease is characterized by abnormal vessels that grow from the choriocapillaris and penetrate Bruch's membrane into the outer retinal space[17]. Detection of CNV depends on the segmentation of three reference planes (Vitreous/ILM, OPL/ONL, and RPE/BM) used to generate three slabs: the inner retina, outer retina, and choriocapillaris.

FIG. 11 shows representative images of dry (panels A1, B1, C1, and D1) and wet AMD (panels A2, B2, C2, and D2) cases. Representative cross sectional B-scan images are depicting segmentation results and angiography data overlay are shown in FIG. 11, panels A1 and A2. Structural information from the OCT angiography scans was used to create retinal thickness (FIG. 11, panels B1 and B2) and RPE-drusen complex (RPEDC) maps (FIG. 11, panels D1 and D2). The retinal thickness map is clinically useful in determining atrophy and exudation. The RPEDC map, representing the size and the volume of drusen, has been correlated with risk of clinical progression [31]. FIG. 12, panels C1 and C2 show the absence and presence of CNV in yellow in cross-sectional and en face composite angiograms, respectively.

Because of the effects of shadowgraphic flow projection, true CNV is difficult to identify in either the composite B-scan or en face angiogram. An automated CNV detection algorithm [23] was used to remove the shadowgraphic projection from the outer retinal slab and display the outer retinal slab separately, clearly displaying the CNV (FIG. 11, panel C2). A composite en face angiogram displaying the two retinal slabs in different colors shows the CNV in relation to the retinal angiogram (FIG. 11, panel C2 and FIG. 13, panel A1). An overlay of this composite angiogram on cross-sectional angiogram shows the depth of the CNV in relation to retinal structures (FIG. 11, panel A2). The size of CNV can be quantified by calculating the area of the vessels present in the outer retinal slab.

Diabetic Retinopathy

Retinal neovascularization (RNV), or growth of new vessels above the ILM, is the hallmark of proliferative diabetic retinopathy (PDR). The presence of RNV is associated with high risk of vision loss and is an indication for treatment with panretinal photocoagulation, which reduces the risk of vision loss [32].

Segmenting along the vitreous/ILM border reveals the RNV in the vitreous slab, distinguishing it from intra-retinal microvascular abnormalities (IRMA), which can be difficult to distinguish clinically from early RNV (for example, the 'PDR without edema' case depicted in column 3 of FIG. 12,). By quantifying the RNV area, one can assess the extent and activity of PDR.

FIG. 12 shows several representative images of from four different DR cases. The first row (FIG. 12, panels A1, A2, A3, and A4) shows color-coded B-scans with subtraction of flow projection artifacts and the segmented planes used for slab segmentation. Presenting the structural and flow information simultaneously clarifies the anatomic relationship between the vessels and the tissue planes. En face composite angiograms of the superficial (FIG. 12, panels B1, B2, B3, and B4) and deep plexus (FIG. 12, panels C1, C2, C3, and C4) (the second and third rows of FIG. 12, respectively) disclose vascular abnormalities including RNV, IRMA, thickening and narrowing of vessels, and capillary drop out in a manner similar to traditional dye-based angiograms.

Capillary nonperfusion is a major feature of DR associated with vision loss and progression of disease [33, 34]. Using an automated algorithm, regions of capillary nonperfusion [16, 17] were identified and quantified. A nonperfusion map was created for each case is presented in FIG. 12, panels D1, D2, D3, and D4) showing blue areas with flow signal lower than 1.2 standard deviations above the mean decorrelation signal in the foveal avascular zone.

It is also possible to generate a retinal thickness map by assessing the distance from vitreous/ILM to RPE/BM across the volumetric scan. Thickness maps are shown in FIG. 12, panels E1, E2, E3, and E4). Such a map allows the clinician to assess the central macula for edema, atrophy, and distortion of contour.

Clinical Evaluation of 6×6 mm Scans

The pathology in AMD and DR extends beyond the central macular area. While OCT angiography cannot match the field of view of the current dye-based widefield techniques [35, 36], 6×6 mm OCT angiography scans cover a wider area, and there for reveal pathology not shown in 3×3 mm scans. FIG. 13, panels A1 and A2 show examples of 6×6 mm scans of the wet AMD case in FIG. 11 and PDR without edema case seen in FIG. 12, respectively. Although these lower resolution scans show fewer details of the capillaries, 6×6 mm scans capture areas of capillary nonperfusion not present in the 3×3 mm scans areas. This is apparent in FIG. 13 by the black areas of capillary drop out located outside the 3×3 mm blue square.

OCT Angiography Image Processing System

FIG. 14 schematically shows an example system 1400 for OCT angiography image processing in accordance with various embodiments. System 1400 comprises an OCT system 1402 configured to acquire an OCT image comprising OCT interferograms and one or more processors or computing systems 1404 that are configured to implement the various processing routines described herein. OCT system 1400 can comprise an OCT system suitable for OCT angiography applications, e.g., a swept source OCT system.

In various embodiments, an OCT system can be adapted to allow an operator to perform various tasks. For example, an OCT system can be adapted to allow an operator to configure and/or launch various ones of the herein described methods. In some embodiments, an OCT system can be adapted to generate, or cause to be generated, reports of various information including, for example, reports of the results of scans run on a sample.

In embodiments of OCT systems comprising a display device, data and/or other information can be displayed for an operator. In embodiments, a display device can be adapted to receive an input (e.g., by a touch screen, actuation of an icon, manipulation of an input device such as a joystick or knob, etc.) and the input can, in some cases, be communicated (actively and/or passively) to one or more processors. In various embodiments, data and/or information can be displayed, and an operator can input information in response thereto.

In some embodiments, the above described methods and processes can be tied to a computing system, including one or more computers. In particular, the methods and processes described herein, e.g., method 1600 described below, can be implemented as a computer application, computer service, computer API, computer library, and/or other computer program product.

FIG. 15 schematically shows a non-limiting computing device 1500 that can perform one or more of the above described methods and processes. For example, computing device 1500 can represent a processor included in system 1400 described above, and can be operatively coupled to, in communication with, or included in an OCT system or OCT image acquisition apparatus. Computing device 1500 is shown in simplified form. It is to be understood that virtually any computer architecture can be used without departing from the scope of this disclosure. In different embodiments, computing device 1500 can take the form of a microcomputer, an integrated computer circuit, printed circuit board (PCB), microchip, a mainframe computer, server computer, desktop computer, laptop computer, tablet computer, home entertainment computer, network computing device, mobile computing device, mobile communication device, gaming device, etc.

Computing device 1500 includes a logic subsystem 1502 and a data-holding subsystem 1504. Computing device 1500 can optionally include a display subsystem 1506, a communication subsystem 1508, an imaging subsystem 1510, and/or other components not shown in FIG. 15. Computing device 1500 can also optionally include user input devices such as manually actuated buttons, switches, keyboards, mice, game controllers, cameras, microphones, and/or touch screens, for example.

Logic subsystem 1502 can include one or more physical devices configured to execute one or more machine-readable instructions. For example, the logic subsystem can be configured to execute one or more instructions that are part of one or more applications, services, programs, routines, libraries, objects, components, data structures, or other logical constructs. Such instructions can be implemented to perform a task, implement a data type, transform the state of one or more devices, or otherwise arrive at a desired result.

The logic subsystem can include one or more processors that are configured to execute software instructions. For example, the one or more processors can comprise physical circuitry programmed to perform various acts described herein. Additionally or alternatively, the logic subsystem can include one or more hardware or firmware logic machines configured to execute hardware or firmware instructions. Processors of the logic subsystem can be single core or multicore, and the programs executed thereon can be configured for parallel or distributed processing. The logic subsystem can optionally include individual components that are distributed throughout two or more devices, which can be remotely located and/or configured for coordinated processing. One or more aspects of the logic subsystem can be virtualized and executed by remotely accessible networked computing devices configured in a cloud computing configuration.

Data-holding subsystem 1504 can include one or more physical, non-transitory, devices configured to hold data and/or instructions executable by the logic subsystem to implement the herein described methods and processes. When such methods and processes are implemented, the state of data-holding subsystem 1504 can be transformed (e.g., to hold different data).

Data-holding subsystem 1504 can include removable media and/or built-in devices. Data-holding subsystem 1504 can include optical memory devices (e.g., CD, DVD, HD-DVD, Blu-Ray Disc, etc.), semiconductor memory devices (e.g., RAM, EPROM, EEPROM, etc.) and/or magnetic memory devices (e.g., hard disk drive, floppy disk drive, tape drive, MRAM, etc.), among others. Data-holding subsystem 1504 can include devices with one or more of the following characteristics: volatile, nonvolatile, dynamic, static, read/write, read-only, random access, sequential access, location addressable, file addressable, and content addressable. In some embodiments, logic subsystem 1502 and data-holding subsystem 1504 can be integrated into one or more common devices, such as an application specific integrated circuit or a system on a chip.

FIG. 15 also shows an aspect of the data-holding subsystem in the form of removable computer-readable storage media 1512, which can be used to store and/or transfer data and/or instructions executable to implement the herein described methods and processes. Removable computer-readable storage media 1512 can take the form of CDs, DVDs, HD-DVDs, Blu-Ray Discs, EEPROMs, flash memory cards, USB storage devices, and/or floppy disks, among others.

When included, display subsystem 1506 can be used to present a visual representation of data held by data-holding subsystem 1504. As the herein described methods and processes change the data held by the data-holding subsystem, and thus transform the state of the data-holding subsystem, the state of display subsystem 1506 can likewise be transformed to visually represent changes in the underlying data. Display subsystem 1506 can include one or more display devices utilizing virtually any type of technology. Such display devices can be combined with logic subsystem 1502 and/or data-holding subsystem 1504 in a shared enclosure, or such display devices can be peripheral display devices.

When included, communication subsystem 1508 can be configured to communicatively couple computing device 1500 with one or more other computing devices. Communication subsystem 1508 can include wired and/or wireless communication devices compatible with one or more different communication protocols. As non-limiting examples, the communication subsystem can be configured for communication via a wireless telephone network, a wireless local area network, a wired local area network, a wireless wide area network, a wired wide area network, etc. In some embodiments, the communication subsystem can allow computing device 1500 to send and/or receive messages to and/or from other devices via a network such as the Internet.

When included, imaging subsystem 1510 can be used acquire and/or process any suitable image data from various sensors or imaging devices in communication with computing device 1500. For example, imaging subsystem 1510 can be configured to acquire OCT image data, e.g., interferograms, as part of an OCT system, e.g., OCT system 1402 described above. Imaging subsystem 1510 can be combined with logic subsystem 1502 and/or data-holding subsystem 1504 in a shared enclosure, or such imaging subsystems can comprise periphery imaging devices. Data received from the imaging subsystem can be held by data-holding subsystem 1504 and/or removable computer-readable storage media 1512, for example.

FIG. 16 shows an example method 1600 for processing a set of B-scans to segment the layers of the retina in accordance with various embodiments. Method 1600 (and methods 1700 and 1800, described below) can be implemented by a system such as system 1400 described above, that includes an OCT system and one or more processors or computing systems, such as computing device 1500 described above. For example, one or more operations described herein can be implemented by one or more processors having physical circuitry programmed to perform the operations. In embodiments, one or more steps of method 1600 can be automatically performed by one or more processors or computing devices. Further, various acts illustrated in FIG. 16 can be performed in the sequence illustrated, in other sequences, in parallel, or in some cases omitted. Method 1600 can be used to enact a workflow for the segmentation of retina layers depicted in a set of structural OCT B-scans.

At 1602, method 1600 includes receiving structural OCT data in the form of one or more B-scans. For example, OCT scan data including a plurality of interferograms can be acquired from a swept-source or other OCT system, e.g., the system shown in FIG. 1400. In other embodiments, the OCT data can be received by a computing device from an OCT scanning system via a network or from a storage medium coupled to or in communication with the computing device.

At 1604, method 1600 includes the selection of an initial B-scan to be processed for segmentation of retinal layer boundaries. The selection at 1602 can be performed automatically by computer algorithm or can involve user interaction to select a suitable B-scan for processing. For example, the user review several B-scans within the plurality of B-scans received in order to identify a B-scan wherein the retinal layers are minimally disrupted by pathology. Alternatively, the initial B-scan can be selected by convention, for example, the first B-scan in the plurality of B-scans received.

At 1606, method 1600 begins a looping procedure to sequentially process the received B-scans. In the example method 1600 depicted, the workflow of the loop begins with automatic segmentation of retinal layers for a given B-scan using the directional graph search method described previously. At 1608, an optional review step is introduced wherein the user can view the segmentation results to determine whether the calculated layer boundaries faithfully represent the retina layers depicted in the B-scan. In an embodiment of workflow, this review step can take place after all B-scans have been auto-segmented, or can take place in a strict step-wise manner. In the case where segmentation results for a given B-scan are deemed acceptable at 1608, the method 1600 proceeds to 1612 and the segmentation results from the given B-scan are propagated to the next B-scan to be processed in the loop such that the results are used to constrain the search space of the directional graph search to be performed on the subsequent B-scan. Once all B-scans have been processed, as determined at 1614, the complete retina boundary segmentation information for the plurality of B-scans is returned at 1616 for use in other methods.

Returning to 1608, for the case where auto-segmentation produces unacceptable segmentation results within a B-scan, method 1600 branches to 1610 wherein manual correction of problematic layers can be performed using the editing tools described previously. Such editing can include re-routing of portions of a given layer boundary to account for the presence of a pathological feature, manual re-delineation of retinal layer boundary or boundaries across the entire width of the B-scan image, etc. As described previously, in an embodiment, once completed these edits to layer segmentation profiles can be propagated across adjacent B-scans to expedite workflow.

FIG. 17 shows an example of a method 1700 to visualize and quantify OCT angiography results. Method 1700 receives a plurality of both structural OCT B-scans and OCT angiography B-scans at 1702. For example, these OCT scan data can be acquired from an OCT system such as the one shown in 1400 or can be received from a computing device associated with an OCT scanning system via a network or from a storage medium coupled to or in communication with the computing device. Method 1700 also receives at 1704 segmented boundary information associated with structural OCT scan received at 1702. This retina layer segmentation information can be provided, for example, by a method such as method 1600 shown in FIG. 16.

At 1706, method 1700 includes an option for selecting a retinal slab or slabs for visualization and quantification operations. In an embodiment, this selection can be enacted by the analyst through the use of an interactive graphical user interface or command line interface. Alternatively, the selection method can be embodied in a program or script-based procedure such that slab and results selection can be effected without direct user interaction.

In the example method 1700, once the slab (or slabs) is selected, several options exist for visualizing or quantifying OCT angiography results. One option, at 1708, is the generation of thickness data for the associated structural OCT slab. This thickness data can be calculated from the bounding surfaces of the slab and presented either as thickness maps as depicted in FIG. 1I and FIGS. 11B and 11D, or exported in a format amenable to further analysis (e.g., in a format spreadsheet-readable format). Another possible option, at 1710, is to present the structural images with angiography (flow) data overlaid such that a composite image is presented. These composite images can be presented in cross section (as shown in FIG. 1A) or as en face maximum projection angiograms (as shown in FIGS. 1J and 1K, for example). A further option for slab data visualization and presentation exemplified in steps 1712, 1714, 1716, and 1718 of method 1700 is the production of 2D en face angiograms (angiography maps) for specific retinal layers. Because OCT imaging is subject to shadowgraphic projection of vascular structures in the A-scan (depth) direction, it is typically necessary to process the angiograms to remove artefactual data. A general procedure outlined in method 1700 entails the generation of initial en face angiograms for different retinal layer slabs at 1712, application of a procedure to remove shadowgraphic projections at 1714 (an example of such a procedure is provided in FIG. 18), followed by quantification of angiogram properties at 1718 and the generation of shadow-corrected angiogram maps at 1718. Examples of initial angiograms are shown in FIGS.

1B-1F; examples of angiograms following removal of shadowgraphic projection are shown in FIGS. 1G and 1J. Depending on the retinal layer visualized, the quantified properties calculated at 1716 can include, for example, vessel density, nonperfusion or capillary dropout area, neovascularization area.

FIG. 18 shows an example of a method 1800 to remove shadowgraphic projection artifacts from outer retina OCT angiograms. At 1802, method 1800 receives structural OCT data and OCT angiography in the form of one or more B-scans. At 1804, a 2D en face maximum projection angiogram is calculated for the outer retina slab, and at 1806 a 2D en face maximum projection angiogram is calculated for the inner retina slab. At 1808, the outer retina angiogram is modified by subtracting from it the inner retina angiogram. At 1810, this modified outer retina angiogram can then be used to remove shadowgraphic projections from the B-scan data comprising the outer retinal slab, thereby improving the quality of angiographic data presented in composite cross sectional images.

It is to be understood that the configurations and/or approaches described herein are exemplary in nature, and that these specific embodiments or examples are not to be considered in a limiting sense, because numerous variations are possible. The specific routines or methods described herein can represent one or more of any number of processing strategies. As such, various acts illustrated can be performed in the sequence illustrated, in other sequences, in parallel, or in some cases omitted. Likewise, the order of the above-described processes can be changed.

The subject matter of the present disclosure includes all novel and nonobvious combinations and subcombinations of the various processes, systems and configurations, and other features, functions, acts, and/or properties disclosed herein, as well as any and all equivalents thereof.

REFERENCES

The following numbered references are cited throughout this disclosure by inclusion of the number reference(s) in square brackets. Each of the following references is hereby incorporated by reference in its entirety.

1. D. Huang, Y. Jia, and S. S. Gao, "Principles of Optical Coherence Tomography Angiography" in *OCT Angiography Atlas* H. D. Lumbros B, Rosenfield P, Chen C, Rispoli M, Romano A, ed. (Jaypee Brothers Medical Publishers, New Delhi, 2015).
2. D. Huang, E. A. Swanson, C. P. Lin, J. S. Schuman, W. G. Stinson, W. Chang, M. R. Hee, T. Flotte, K. Gregory, C. A. Puliafito, and et al., "Optical coherence tomography," Science 254, 1178-1181 (1991).
3. L. An, and R. K. Wang, "In vivo volumetric imaging of vascular perfusion within human retina and choroids with optical micro-angiography," Optics Express 16, 11438-11452 (2008).
4. I. Grulkowski, I. Gorczynska, M. Szkulmowski, D. Szlag, A. Szkulmowska, R. A. Leitgeb, A. Kowalczyk, and M. Wojtkowski, "Scanning protocols dedicated to smart velocity ranging in spectral OCT," Opt Express 17, 23736-23754 (2009).
5. Y. Yasuno, Y. Hong, S. Makita, M. Yamanari, M. Akiba, M. Miura, and T. Yatagai, "In vivo high-contrast imaging of deep posterior eye by 1-microm swept source optical coherence tomography and scattering optical coherence angiography," Opt Express 15, 6121-6139 (2007).
6. J. Fingler, R. J. Zawadzki, J. S. Werner, D. Schwartz, and S. E. Fraser, "Volumetric microvascular imaging of human retina using optical coherence tomography with a novel motion contrast technique," Opt Express 17, 22190-22200 (2009).
7. G. Liu, W. Qi, L. Yu, and Z. Chen, "Real-time bulk-motion-correction free Doppler variance optical coherence tomography for choroidal capillary vasculature imaging," Opt Express 19, 3657-3666 (2011).
8. Y. Jia, O. Tan, J. Tokayer, B. Potsaid, Y. Wang, J. J. Liu, M. F. Kraus, H. Subhash, J. G. Fujimoto, J. Hornegger, and D. Huang, "Split-spectrum amplitude-decorrelation angiography with optical coherence tomography," Optics Express 20, 4710-4725 (2012).
9. S. S. Gao, G. Liu, D. Huang, and Y. Jia, "Optimization of the split-spectrum amplitude-decorrelation angiography algorithm on a spectral optical coherence tomography system," Optics Letters 40, 2305-2308 (2015).
10. M. P. Lopez-Saez, E. Ordoqui, P. Tornero, A. Baeza, T. Sainza, J. M. Zubeldia, M. L. Baeza, and M. L. Baeza, "Fluorescein-Induced Allergic Reaction," Annals of Allergy, Asthma & Immunology 81, 428-430 (1998).
11. R. K. Wang, S. L. Jacques, Z. Ma, S. Hurst, S. R. Hanson, and A. Gruber, "Three dimensional optical angiography," Optics Express 15, 4083-4097 (2007).
12. L. Liu, Y. Jia, H. L. Takusagawa, A. D. Pechauer, B. Edmunds, L. Lombardi, E. Davis, J. C. Morrison, and D. Huang, "Optical coherence tomography angiography of the peripapillary retina in glaucoma," JAMA Ophthalmology (2015).
13. Y. Jia, E. Wei, X. Wang, X. Zhang, J. C. Morrison, M. Parikh, L. H. Lombardi, D. M. Gattey, R. L. Armour, B. Edmunds, M. F. Kraus, J. G. Fujimoto, and D. Huang, "Optical Coherence Tomography Angiography of Optic Disc Perfusion in Glaucoma," Ophthalmology 121, 1322-1332 (2013).
14. A. D. Pechauer, Y. Jia, L. Liu, S. S. Gao, C. Jiang, and D. Huang, "Optical Coherence Tomography Angiography of Peripapillary Retinal Blood Flow Response to Hyperoxia," Invest Ophthalmol Vis Sci 56, 3287-3291 (2015).
15. A. Ishibazawa, T. Nagaoka, A. Takahashi, T. Omae, T. Tani, K. Sogawa, H. Yokota, and A. Yoshida, "Optical Coherence Tomography Angiography in Diabetic Retinopathy: A Prospective Pilot Study," American journal of ophthalmology (2015).
16. Y. Jia, S. T. Bailey, T. S. Hwang, S. M. McClintic, S. S. Gao, M. E. Pennesi, C. J. Flaxel, A. K. Lauer, D. J. Wilson, and J. Hornegger, "Quantitative optical coherence tomography angiography of vascular abnormalities in the living human eye," Proceedings of the National Academy of Sciences 112, E2395-E2402 (2015).
17. Y. Jia, S. T. Bailey, D. J. Wilson, O. Tan, M. L. Klein, C. J. Flaxel, B. Potsaid, J. J. Liu, C. D. Lu, and M. F. Kraus, "Quantitative optical coherence tomography angiography of choroidal neovascularization in age-related macular degeneration," Ophthalmology 121, 1435-1444 (2014).
18. T. S. Hwang, Y. Jia, S. S. Gao, S. T. Bailey, A. K. Lauer, C. J. Flaxel, D. J. Wilson, and D. Huang, "Optical Coherence Tomography Angiography Features of Diabetic Retinopathy," Retina (in press).
19. P. Teng, "Caserel—An Open Source Software for Computer-aided Segmentation of Retinal Layers in Optical Coherence Tomography Images," (2013).
20. P. P. Srinivasan, S. J. Heflin, J. A. Izatt, V. Y. Arshaysky, and S. Farsiu, "Automatic segmentation of up to ten layer boundaries in SD-OCT images of the mouse retina with and without missing layers due to pathology," Biomedical Optics Express 5, 348-365 (2014).

21. S. J. Chiu, X. T. Li, P. Nicholas, C. A. Toth, J. A. Izatt, and S. Farsiu, "Automatic segmentation of seven retinal layers in SDOCT images congruent with expert manual segmentation," Optics Express 18, 19413-19428 (2010).
22. X. Yin, J. R. Chao, and R. K. Wang, "User-guided segmentation for volumetric retinal optical coherence tomography images," Journal of Biomedical Optics 19, 086020-086020 (2014).
23. L. Liu, S. S. Gao, S. T. Bailey, D. Huang, D. Li, and Y. Jia, "Automated choroidal neovascularization detection algorithm for optical coherence tomography angiography," Biomedical Optics Express 6, 3564-3576 (2015).
24. E. N. Mortensen, and W. A. Barrett, "Intelligent scissors for image composition," in *Proceedings of the 22nd annual conference on Computer graphics and interactive techniques* (ACM, 1995), pp. 191-198.
25. D. Pope, D. Parker, D. Gustafson, and P. Clayton, "Dynamic search algorithms in left ventricular border recognition and analysis of coronary arteries," in *IEEE Proceedings of Computers in Cardiology* (1984), pp. 71-75.
26. X. Liu, D. Z. Chen, M. H. Tawhai, X. Wu, E. A. Hoffman, and M. Sonka, "Optimal Graph Search Based Segmentation of Airway Tree Double Surfaces Across Bifurcations," Medical Imaging, IEEE Transactions on 32, 493-510 (2013).
27. M. B. Merickel Jr, M. D. Abràmoff, M. Sonka, and X. Wu, "Segmentation of the optic nerve head combining pixel classification and graph search," in *Medical Imaging* (International Society for Optics and Photonics, 2007), pp. 651215-651215-651210.
28. M. K. Garvin, M. D. Abràmoff, R. Kardon, S. R. Russell, X. Wu, and M. Sonka, "Intraretinal layer segmentation of macular optical coherence tomography images using optimal 3-D graph search," Medical Imaging, IEEE Transactions on 27, 1495-1505 (2008).
29. X. Chen, M. Niemeijer, L. Zhang, K. Lee, M. D. Abràmoff, and M. Sonka, "Three-dimensional segmentation of fluid-associated abnormalities in retinal OCT: probability constrained graph-search-graph-cut," Medical Imaging, IEEE Transactions on 31, 1521-1531 (2012).
30. M. F. Kraus, B. Potsaid, M. A. Mayer, R. Bock, B. Baumann, J. J. Liu, J. Hornegger, and J. G. Fujimoto, "Motion correction in optical coherence tomography volumes on a per A-scan basis using orthogonal scan patterns," Biomedical Optics Express 3, 1182-1199 (2012).
31. S. Farsiu, S. J. Chiu, R. V. O'Connell, F. A. Folgar, E. Yuan, J. A. Izatt, and C. A. Toth, "Quantitative Classification of Eyes with and without Intermediate Age-related Macular Degeneration Using Optical Coherence Tomography," Ophthalmology 121, 162-172 (2014).
32. D. R. S. R. Group, "Photocoagulation treatment of proliferative diabetic retinopathy: clinical application of Diabetic Retinopathy Study (DRS) findings, DRS Report Number 8," Ophthalmology 88, 583-600 (1981).
33. E. T. D. R. S. R. Group, "Early Treatment Diabetic Retinopathy Study design and baseline patient characteristics: ETDRS report number 7," Ophthalmology 98, 741-756 (1991).
34. M. S. Ip, A. Domalpally, J. K. Sun, and J. S. Ehrlich, "Long-term effects of therapy with ranibizumab on diabetic retinopathy severity and baseline risk factors for worsening retinopathy," Ophthalmology 122, 367-374 (2015).
35. S. Kiss, and T. L. Berenberg, "Ultra Widefield Fundus Imaging for Diabetic Retinopathy," Current diabetes reports 14, 1-7 (2014).
36. P. S. Silva, J. D. Cavallerano, N. M. N. Haddad, H. Kwak, K. H. Dyer, A. F. Omar, H. Shikari, L. M. Aiello, J. K. Sun, and L. P. Aiello, "Peripheral lesions identified on ultrawide field imaging predict increased risk of diabetic retinopathy progression over 4 years," Ophthalmology 122, 949-956 (2015).

The invention claimed is:

1. A method of editing a retina layer boundary segmentation comprising:
   receiving a set of structural OCT B-scans;
   segmenting the retinal layer boundaries of the structural OCT B-scans by the steps of:
   a) receiving a set of relative retinal layer thickness data;
   b) enhancing intensity transition in the structural OCT B-scan images;
   c) selectin a first B-scan image from the set of structural OCT B-scans;
   d) selecting a first retinal layer boundary in the first B-scan image;
   e) applying a directional graph search to the first retinal layer boundary, thereby generating a first segmented retinal layer boundary;
   f) selecting a second retinal layer boundary on the first B-scan image;
   g) constraining a search region of the second retinal layer boundary using the first segmented retinal layer boundary and the set of relative retinal layer thickness data; and
   h) applying a directional graph search to the second retinal layer boundary; thereby generating a second segmented retinal layer boundary; thereby generating a set of segmented retinal layer boundaries;
   reviewing the set of segmented retinal layer boundaries;
   selecting a segmented retinal layer boundary in a B-scan;
   editing the segmented retinal layer boundary in a B-scan using an intelligent scissors tool based on directed graph search, or a portion thereof, thereby creating a new retinal layer boundary segmentation; and
   propagating the new retinal layer boundary segmentation to adjacent structural OCT B-scans.

2. A method of analyzing OCT angiography data comprising:
   receiving a set of structural OCT B-scans;
   receiving a set of OCT angiography B-scans;
   segmenting the retina layers in the structural OCT B-scans, by the steps of:
   a) receiving a set of relative retinal layer thickness data;
   b) enhancing intensity transition in the structural OCT B-scan images;
   c) selecting a first B-scan image from the set of structural OCT B-scans;
   d) selecting a first retinal layer boundary in the first B-scan image;
   e) applying a directional graph search to the first retinal layer boundary, thereby generating a first segmented retinal layer boundary;
   f) selecting a second retinal layer boundary on the first B-scan image;
   g) constraining a search region of the second retinal layer boundary using the first segmented retinal layer boundary and the set of relative retinal layer thickness data; and
   applying a directional graph search to the second retinal layer boundary; thereby generating a second segmented retinal layer boundary: thereby generating a set of segmented retina layer boundaries;

defining a retinal layer slab, wherein the upper and lower extents of the retinal layer slab are defined using the segmented retina layer boundaries;

color-coding flow data from the set of OCT angiography B-scans based on the retinal layer slab in which it resides;

merging the color-coded flow data from the set of OCT angiography B-scans with structural OCT data from the set of structural OCT B-scans, thereby generating composite OCT data;

presenting composite OCT data.

3. The method of claim 2 wherein presenting the composite OCT data comprises generation of a color-coded 2D en face angiogram.

* * * * *